US010436779B2

(12) United States Patent
Zourob

(10) Patent No.: US 10,436,779 B2
(45) Date of Patent: Oct. 8, 2019

(54) BIOSENSOR USING MAGNETIC PARTICLES FOR PATHOGEN DETECTION

(71) Applicant: Mohammed Zourob, Riyadh (SA)

(72) Inventor: Mohammed Zourob, Riyadh (SA)

(73) Assignee: Alfaisal University, Riyadh (SA)

( * ) Notice: Subject to any disclaimer, the term of this patent is extended or adjusted under 35 U.S.C. 154(b) by 366 days.

(21) Appl. No.: 14/867,353

(22) Filed: Sep. 28, 2015

(65) Prior Publication Data

US 2017/0038373 A1    Feb. 9, 2017

Related U.S. Application Data

(63) Continuation-in-part of application No. 14/819,195, filed on Aug. 5, 2015, now Pat. No. 10,337,047.

(51) Int. Cl.
*G01N 33/543* (2006.01)
*G01N 33/569* (2006.01)

(52) U.S. Cl.
CPC . *G01N 33/54333* (2013.01); *G01N 33/56911* (2013.01); *G01N 2333/21* (2013.01); *G01N 2333/245* (2013.01); *G01N 2333/31* (2013.01); *G01N 2333/952* (2013.01)

(58) Field of Classification Search
CPC ........... G01N 33/558; G01N 33/56911; G01N 2035/00762; G01N 21/78; G01N 30/91; G01N 33/54306; G01N 33/54326; G01N 33/54333; G01N 33/585; G01N 2333/21; G01N 2333/31; G01N 2333/952; G01N 2333/245; Y10S 435/97; Y10S 435/805; Y10S 435/969; B01L 2300/0825; B01L 2400/0406; B01L 2200/0668; B01L 2400/043

See application file for complete search history.

(56) References Cited

U.S. PATENT DOCUMENTS

2015/0244852 A1* 8/2015 Erickson ................ G01N 21/31
455/557

OTHER PUBLICATIONS

Wang et al. Materials 2013, 6, 5690-5699.*
Veiseh et al. Langmuir 2002, 18, 6671-6678.*

* cited by examiner

*Primary Examiner* — Sally A Merkling
(74) *Attorney, Agent, or Firm* — Geeta Kadambi; Riddhi IP LLC

(57) ABSTRACT

There is provided a biosensor for detecting pathogens in a sample. The detection is based on colorimetry. The biosensor comprises one or more particle supports and a magnetic material attached to a planar support. The biosensor embodies magnetic particles that are functionalized using a chemical substrate specific to the pathogens to be detected. The sensor may allow for a simultaneous detection of a plurality of pathogens in the sample. Also, the sensor may be disposable. Moreover, the sensor may be integrated in a portable detection device.

13 Claims, 19 Drawing Sheets

Specification includes a Sequence Listing.

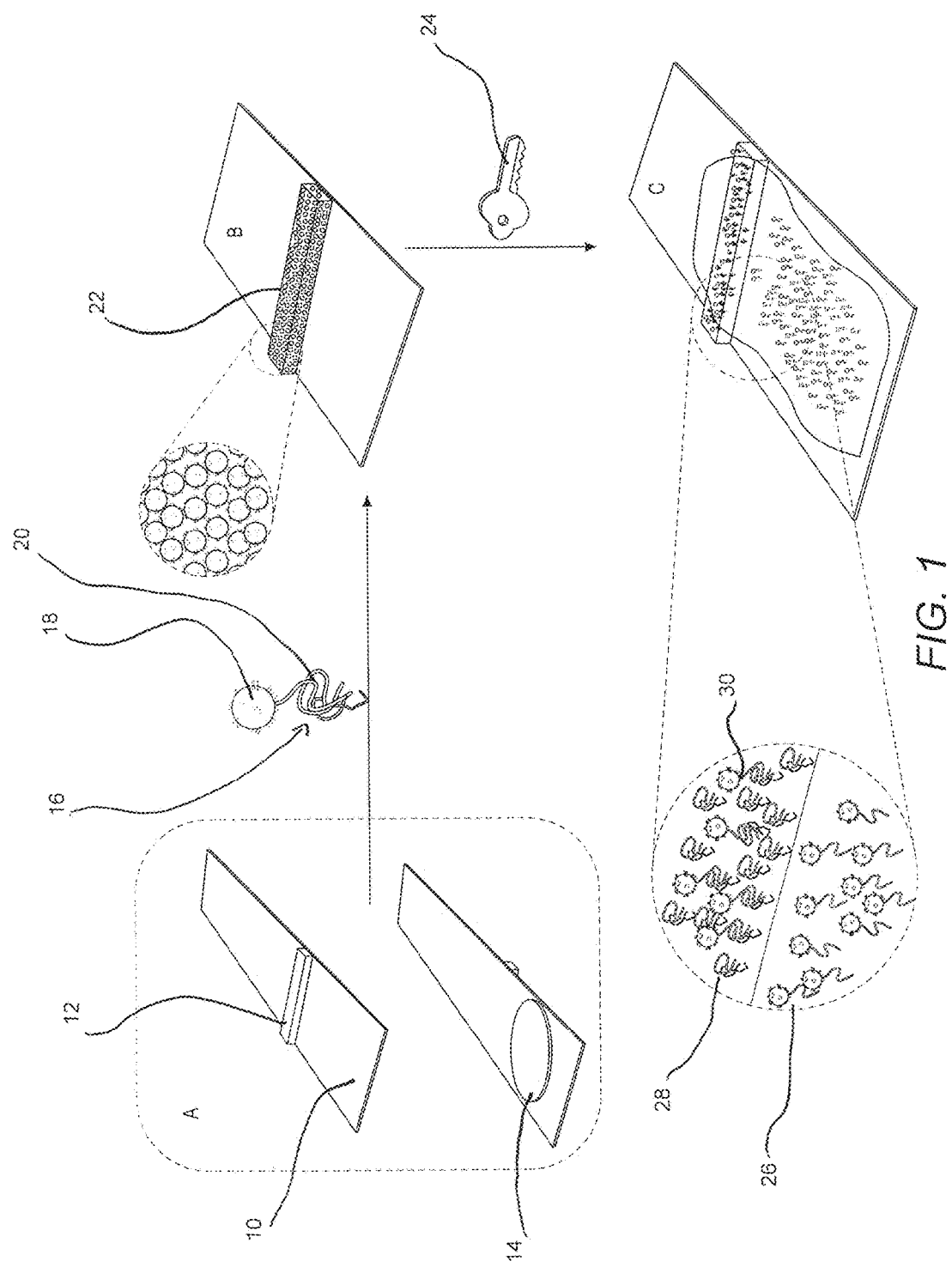

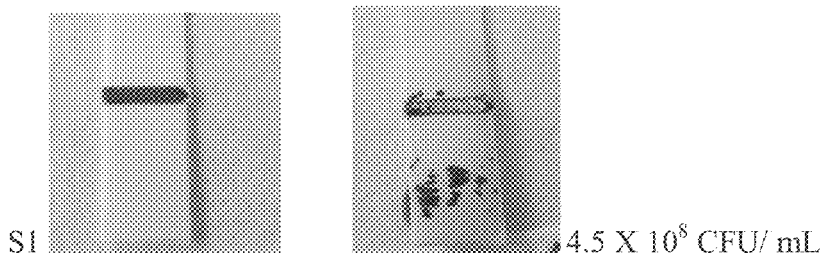
S1
FIG. 4A  FIG. 4B  4.5 X $10^8$ CFU/mL
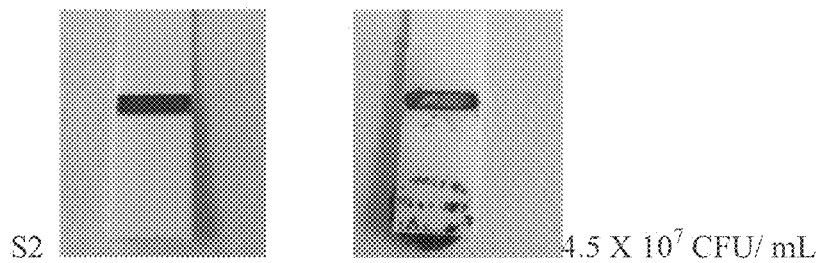
S2
FIG. 4C  FIG. 4D  4.5 X $10^7$ CFU/mL
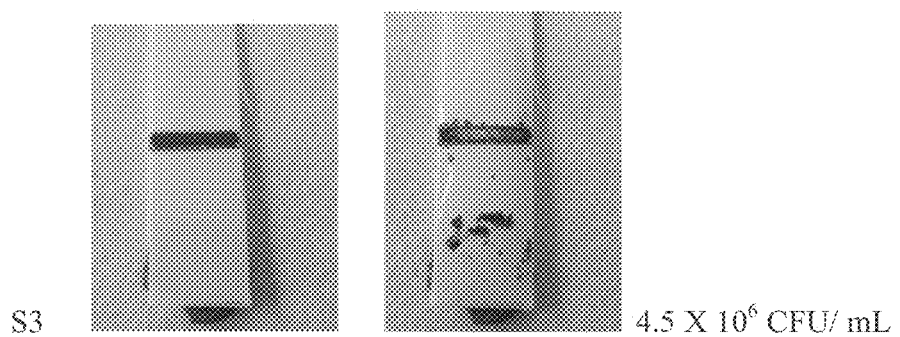
S3
FIG. 4E  FIG. 4F  4.5 X $10^6$ CFU/mL
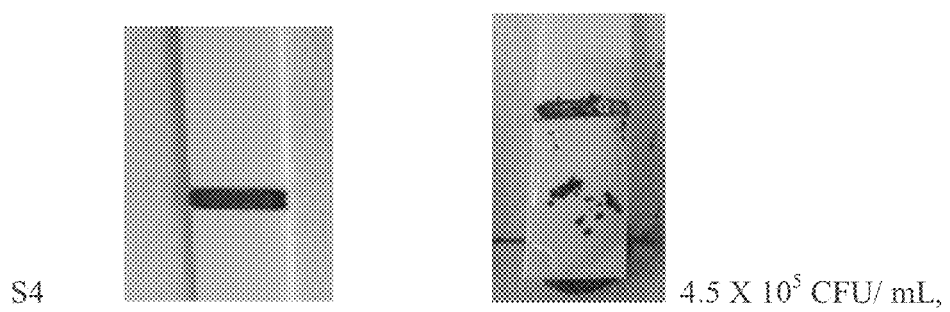
S4
FIG. 4G  FIG. 4H  4.5 X $10^5$ CFU/mL,

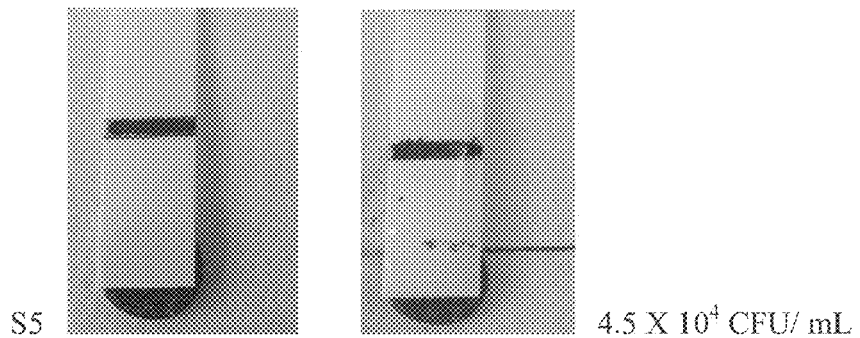
S5  FIG. 4I   FIG. 4J   4.5 X 10⁴ CFU/ mL
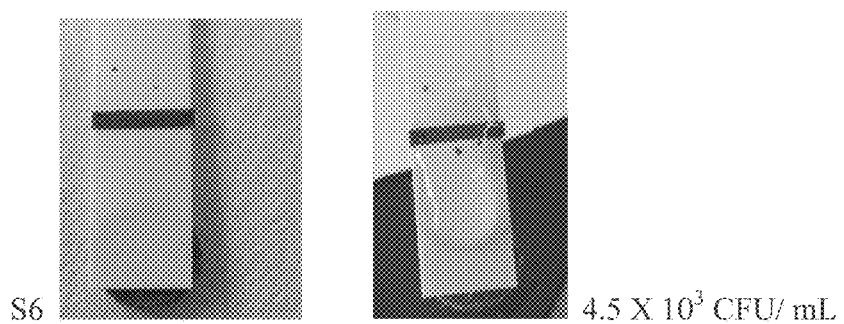
S6  FIG. 4K   FIG. 4L   4.5 X 10³ CFU/ mL
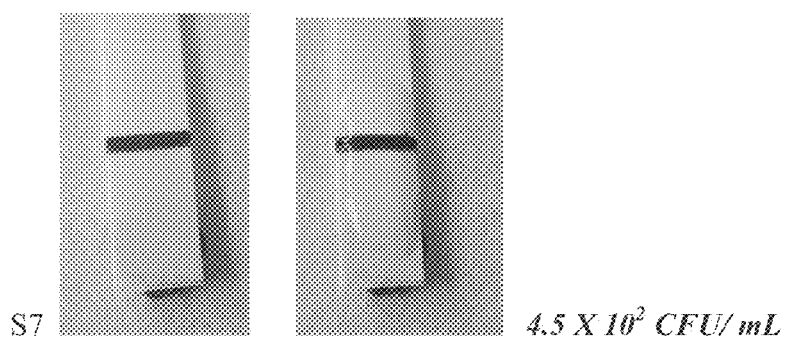
S7  FIG. 4M   FIG. 4N   *4.5 X 10² CFU/ mL*

Blank
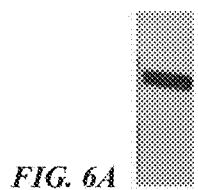
FIG. 6A
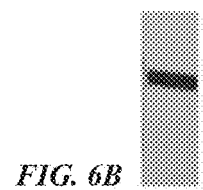
FIG. 6B
Lettuce
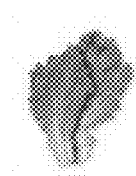
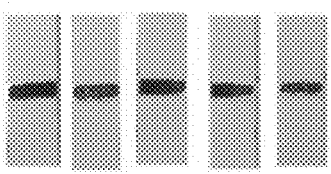
FIG. 6C
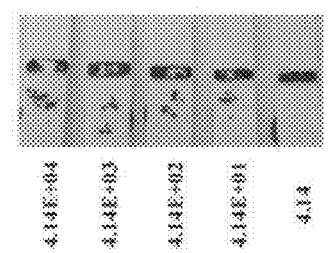
FIG. 6D
Turkey
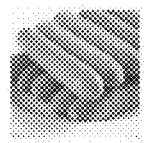
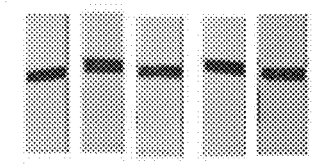
FIG. 6E
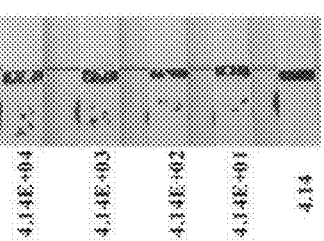
FIG. 6F
Ground Beef
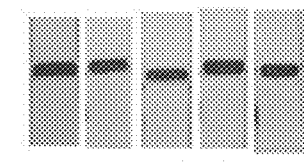
FIG. 6G
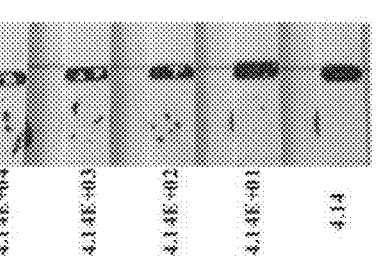
FIG. 6H
Milk
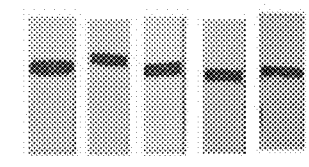
FIG. 6I
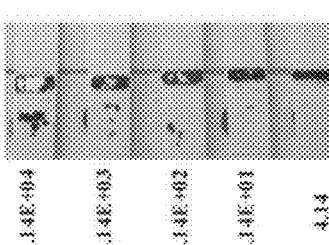
FIG. 6J Negative Blank
(Unspiked
environmental
samples)   *FIG. 7A* 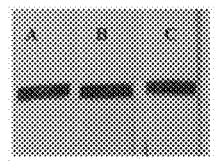   *FIG. 7B* 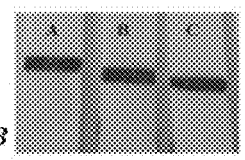
Hospital Intensive
Care Unit
          *FIG. 7C* 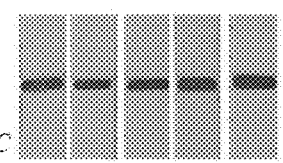   *FIG. 7D* 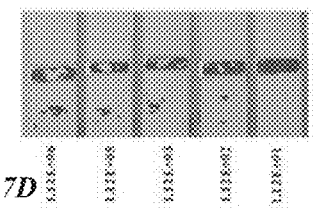
Hospital stairs
          *FIG. 7E* 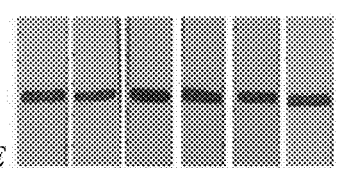   *FIG. 7F* 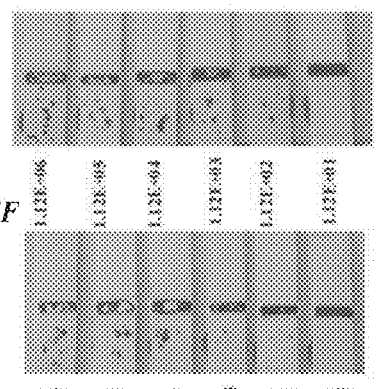
University
courtyard
          *FIG. 7G* 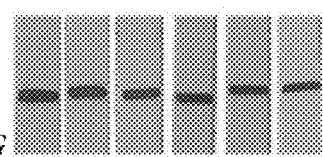   *FIG. 7H* 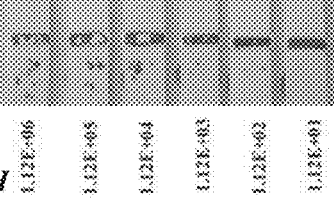

*Listeria monocytogenesis*

*P. aeraginosa*

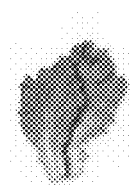
Lettuce
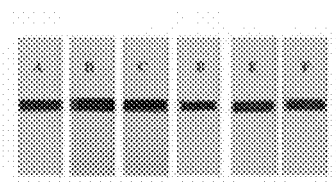
*FIG. 12A*
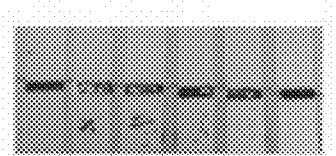
*FIG. 12B*
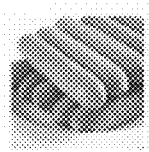
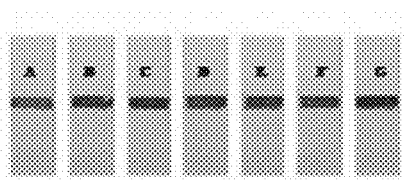
*FIG. 12C*
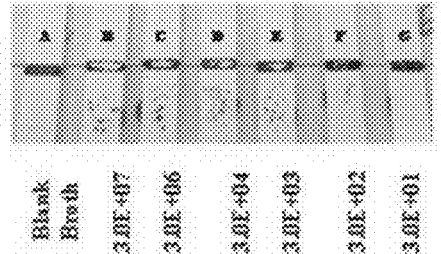
*FIG. 12D*
Turkey Sausage
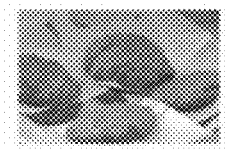
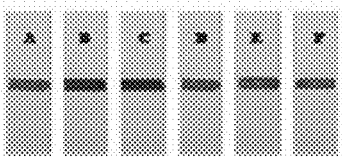
*FIG. 12E*
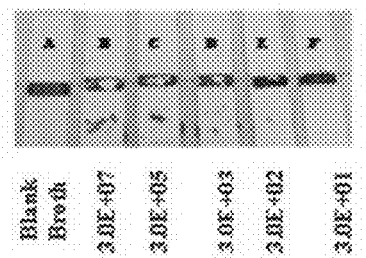
*FIG. 12F*
Ground Beef
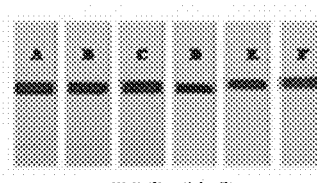
*FIG. 12G*
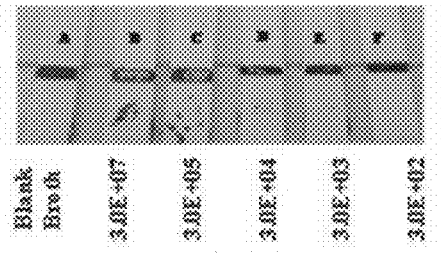
*FIG. 12H*
Milk

SEQUENCE LISTING

```
<160> NUMBER OF SEQ ID NOS: 8

<210> SEQ ID NO 1
<211> LENGTH: 20
<212> TYPE: PRT
<213> ORGANISM: Escherichia coli
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 1

Asn His Ala His Xaa Gly Leu Tyr Gly Leu Tyr Gly Leu Tyr Ala His
1               5                   10                  15

Xaa Cys Tyr Ser
            20
```

```
<210> SEQ ID NO 2
<211> LENGTH: 23
<212> TYPE: PRT
<213> ORGANISM: Escherichia coli
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 2

Asn His Ala His Xaa Glu Thr Lys Val Glu Glu Asn Glu Ala Ile Gln
1               5                   10                  15

Lys Ala His Xaa Cys Tyr Ser
            20

<210> SEQ ID NO 3
<211> LENGTH: 12
<212> TYPE: PRT
<213> ORGANISM: Escherichia coli

<400> SEQUENCE: 3

Glu Thr Lys Val Glu Glu Asn Glu Ala Ile Gln Lys
1               5                   10

<210> SEQ ID NO 4
<211> LENGTH: 33
<212> TYPE: PRT
<213> ORGANISM: Escherichia coli
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 4

Asn His Ala His Xaa Lys Val Ser Arg Arg Arg Arg Arg Gly Gly Asp
1               5                   10                  15

Lys Val Asp Arg Arg Arg Arg Arg Gly Gly Asp Ala His Xaa Cys Tyr
            20                  25                  30

Ser

<210> SEQ ID NO 5
<211> LENGTH: 23
<212> TYPE: PRT
<213> ORGANISM: Escherichia coli
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 5

Asn His Ala His Xaa Glu Thr Lys Val Glu Glu Asn Glu Ala Ile Gln
1               5                   10                  15

Lys Ala His Xaa Cys Tyr Ser
            20
```

```
<210> SEQ ID NO 6
<211> LENGTH: 14
<212> TYPE: PRT
<213> ORGANISM: Escherichia coli
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 6

Asn His Ala His Xaa Gly Gly Gly Ala His Xaa Cys Tyr Ser
1               5                   10

<210> SEQ ID NO 7
<211> LENGTH: 23
<212> TYPE: PRT
<213> ORGANISM: Escherichia coli
<220> FEATURE:
<221> NAME/KEY: misc_feature
<222> LOCATION: (3)..(3)
<223> OTHER INFORMATION: Xaa can be any naturally occurring amino acid

<400> SEQUENCE: 7

Ala His Xaa Asn Met Leu Ser Glu Val Glu Arg Glu Ser Gly Ser Gly
1               5                   10                  15

Ser Gly Ser Gly Ser Gly Ser
            20

<210> SEQ ID NO 8
<211> LENGTH: 23
<212> TYPE: PRT
<213> ORGANISM: Escherichia coli
<220> FEATURE:
<221> NAME/KEY: misc_feature
<222> LOCATION: (3)..(3)
<223> OTHER INFORMATION: Xaa can be any naturally occurring amino acid

<400> SEQUENCE: 8

Ala His Xaa Asn Met Leu Ser Glu Val Glu Arg Glu Ser Gly Ser Gly
1               5                   10                  15

Ser Gly Ser Gly Ser Gly Ser
            20
```

BIOSENSOR USING MAGNETIC PARTICLES FOR PATHOGEN DETECTION

CROSS REFERENCE TO RELATED APPLICATION

This application claims priority to pending patent application Ser. No. 14/819,195 filed on 5 Aug. 2015 and is a continuation-in-part of the said application. The pending U.S. application Ser. No. 14/819,195 is hereby incorporated by reference in its entireties for all of its teachings. This application contains sequence listing that has been submitted as an ASCII file named RIPLLC032005US1SEQFILEST25, the date of creation May 16, 2016, and the size of the ASCII text file in bytes is 4 kb.

FIELD OF TECHNOLOGY

This disclosure relates generally to biosensors for detecting pathogens in a sample. More specifically, this disclosure relates to a colorimetric biosensor that uses magnetic particles for detecting pathogens in a sample. The sensor of this disclosure may allow for a simultaneous detection of a plurality of pathogens in the sample. Also, the sensor may be disposable. Moreover, the sensor may be integrated in a portable detection device.

BACKGROUND

The detection of pathogens is critical to the prevention and identification of problems related to health and safety. It is important to obtain analytical results in the shortest time possible. This is not always possible with traditional pathogen detection methods. The advent of new technologies including the use of biosensors has led to promising results.

Various pathogens are known that are potentially harmful to humans. These pathogens include but are not limited to the following that are studied in this disclosure: *Pseudomonas aeruginosa, Staphyloccocus aureus, Escherichia coli, Porphyromonas gingivalis, Listeria monocytogens*. Below is background information for these pathogens in relation to health and safety.

*Pseudomonas aeruginosa (P. aeruginosa)*

*Pseudomonas aeruginosa (P. aeruginosa)* is an aerobic non-fermenting, motile, gram negative rod commonly found free in moist environment, in human skin and gut as a normal flora (Warburton D W et al., 1994). However, *P. aeruginosa* is considered one of the most common pathogens of plant, animal and human (Sherris J C, 1990). It can be postulated in the pathogenesis of many nosocomial pneumonia, urinary tract infection, wound infection and gram-negative bacteremia (National Nosocomial Infection Surveillance (NNIS) system report, 1992-2003). Serious morbidity and mortality were reported in 18-61% of severe pseudomonas infections, mainly attributed to a delay in the diagnosis and inappropriate treatment (Fujitani S et al., 2011). *P. aeruginosa* infection is considered the commonest pathogen infecting the airways of cystic fibrosis patients (Cystic Fibrosis Foundation Annual Patient Registry 2010). *P. aeruginosa* has panoply of virulent factors including toxins and surface components (Somerville G, 1999), in both animals and humans, two modes of virulence expression, and two different pathogenetic performance. One chronic, indolent colonization and another acute invasion with associated septic shock and death especially in immunocompromised hosts. Chronic *P. aeruginosa* infection in patients with cystic fibrosis is associated with an expression of a mucoid phenotype together with down regulation of virulent factors (Zhao J, 2012). Acute invasive *P. aeruginosa* infections is mediated through exotoxins (A, S, and U), elastase (LasA and Lasb), alkaline protease, cytotoxins, phospholipase C, phenazines and cell bound organelles (pili, flagella, and membrane bound lipopolysaccharide) (Mahajan-Miklos S, 1999). Antibiotic resistance by *P. aeruginosa* develops through expression of a beta-lactamase or efflux pumps and down regulation of outer membrane porins (Anderson D J et al., 2012).

Specific detection of proteases secreted by the pathogenic organism under control als rhl qurorum sensing, is a promising target for the analysis of wound infection. Protease based detection methods for diagnosing bacterial infection has been previously described (Sun H et al., 2012; Rittich B et al., 2006). It was founded as most sensitive and specific method used as a screening test for bacterial infection detection. Conventional isolation method for isolating and identifying *Pseudomonas aeruginosa* required 24-96 hours. As a result, crucial time in the management of inflicted patient especially in cases with severe sepsis lead to empirical use of antibiotics which is inappropriate in high number of the cases has led to the emerge of multidrug resistant pathogens and threatened patient life's. Current methods for rapid identification of pseudomonas require advanced automated machine to be operated by highly skilled technicians.

Nanotechnology with magnetic nano and microparticles have received significant attention in recent two decades. They provide broad opportunities for application in chemistry, biochemistry, biology, and medicine. The magnetic nanoparticles (MNPs) have a wide range of highly specific surface area and controlled under the external magnetic field, with high sensitivity, high specificity, low back ground and easy for quantitative analysis. The combined use of magnetic particles technology for the development of efficient biosensors for clinical purposes as diagnostic tool is emerging trends (Tang Y et al., 2014).

*Staphylococcus aureus (S. aureus)*

*Staphylococcus aureus (S. aureus)* is a facultative anaerobic, gram-positive bacterium discovered by Dr. Alexander Ogston in 1880 (Ogston A, 1984). In recent years, *S. aureus* received a lot of attention as it is among the top five common pathogens associated with food-borne illnesses nationwide and one of the most commonly isolated pathogens in hospital-acquired infections (Swartz M N, 1994) and healthcare facilities (Wang C H et al., 2011). *S. aureus* is found in the nostrils and on the skin of warm-blooded animals, including humans and thus can contaminate food products that are derived from animals such as meat, milk and eggs (Yang H, 2011). Also poor hygiene by food handlers during processing and preparation could also contaminate foods (Goto M et al., 2007). What's more, *S. aureus* could live in harsh environments. Thus, under temperature-abused conditions, it can grow and produces enteric toxins. These enterotoxins are heat stable and resistant to the processing and normal cooking temperatures, which usually inactivates or kills the bacterial cells and so causes staphylococcal food poisoning (SFP) (Doyle M P et al., 2007) which is marked by severe gastrointestinal symptoms such as emesis, diarrhea, and/or abdominal pain after a four hour incubation period. Recently, the Center for Disease Control and Prevention (CDC) estimates 240,000 illnesses with 1,000 hospitalizations and 6 deaths associated with staphylococcal food poisoning annually (Scallan E et al., 2011).

*S. aureus* usually colonizeopen wounds and urinary tracts leading to numerous illnesses, from minor skin infections to life-threatening diseases, such as abscesses (Kapral F A et al., 1980), pneumonia (Robertson L et al., 1958), meningitis (Gordon J J et al., 1985), endocarditis (Fowler V G et al., 2007) and septicemia Cross A S et al., 1983). The National Institutes of Health and Centers for Disease Control and Prevention reported 94,000 life-threatening antibiotic-resistant infection cases out of 500,000 people infected with *S. aureus* in United States of America annually (Klein E et al., 2007).

Conventionally, *S. aureus* detection and identification is based on bacterial culture methodology (Bocher S et al., 2008). However, this process is time-consuming, labor-intensive and can take up to several days for identification of the pathogenic bacteria which is an unacceptable delay in emergency and critically illness situations such as sepsis. Thus, this protocol always limits its practical application for rapid clinical diagnosis (Gilbert G L et al., 2002). Other ultra-sensitive detection methods are based on nucleic acid amplification, such as polymerase chain reaction (PCR) (Cheng J C et al., 2006), ligase chain reaction (LCR) (Moore D F et al., 1998) and strand displacement amplification (SDA) (Edman C F et al., 2000) have been employed. Fortunately, these technologies are capable of detecting low numbers of bacterial cells but within several hours. Moreover, these technologies are expensive and require complex procedures such as, prior bacterial DNA isolation, preparation of enzyme reaction mix and expensive instruments for nucleic acid amplification. Accordingly, their use in clinical diagnosis is limited. Other alternative detection methods such as antibody-based immunoassays were well established and have been used Swaminathan B et al., 1994). However, since antibodies are proteins which cannot be amplified, ultrasensitive detection is limited. Nevertheless, this limitation was circumvented by the development of immuno-PCR assay. In this technology, antibody is cross-linked with DNA "barcode" for PCR amplification (Huang S H et al., 2004). However, antibody-DNA complexes conjugation and purification is a daunting task. In addition to the urgent need for expensive instruments. Notomi T et al. (2000), developed a loop-mediated isothermal amplification (LAMP) assay targeting the arcC gene of *S. Aureus* (Lim K T et al., 2013). This assay was equally specific to PCR with a shorter detection time. Recently, Chang Y C et al. (2013) reported the development of a non-PCR-based method which combines aptamer-conjugated gold nanoparticles and a resonance light-scattering detection system. This method successfully detects a single *S. aureus* cell within 1.5 hours. Notably, none of the above mentioned detection methods fully satisfies the detection performance criteria since they are sophisticated, costly in terms of time and money and involves burdensome preparatory steps and sophisticated instruments. Therefore, there is a great need to develop a "sample-to-answer" highly specific and sensitive detection and diagnostic method that can be performed within a short period.

*Escherichia coli (E. coli)*

In recent years, outbreaks of foodborne diseases associated with pathogenic *E. coli* have widely spread and grown as apublic health problem. Traditional and currentdetection techniques of food microbial pathogensare time-consuming, require expensive instrumentation and are labor intensive.

Food borne illness linked to the consumption of fresh and minimally processed food cause a myriad of discomfort and economic loss for many people each year (Shriver-Lake et al., 2007; Beuchat L R et al., 2002; Tauxe R et al., 1997). In general, washing fresh fruits and vegetables with cold water removes lingering dirt present on the surface but does not remove pathogens that may exist inside. Fresh products might be contaminated with microbial pathogens upon contact with contaminated water or manure from the soil (Ingham S C et al., 2004; Song I et al., 2006). A current report has showed that the United States Department of Food Safety and Inspection Services (FSIS) spend over half a billion dollars annually on food inspections for bacterial contaminants. As approximately 73000 food borne infections cases occur every year, out of which 2-7% of these cases suffers from a severe complication called hemolytic uremic syndrome (HUS) (Griffin D W et al., 2003).

Obviously, improvements of food borne pathogens identification techniques after ingestion are important for treatment, but it is more important to prevent infections. One way of doing so is to identify contaminated food products prior to ingestion, preferably before it is distributed to grocery stores, restaurants and manufacturing facilities. This could be achieved through the development of a detection device applicable at the retail level to protect the consumer.

Today, several conventional techniques are used to detect pathogenic microbes: culturing method is commonly used but remain problematic due to the lack of phenotypic characteristics which distinguish between generic pathogens (Gould G et al., 2009), DNA-based assays are currently the most specific and sensitive test available as a confirmatory assay (Uttamchandani M et al., 2009; Call D et al., 2005; Simpson J M et al., 2005; Deisingh A K et al., 2004). However, in these assays long time (up to 48 h) is required to obtain results due to the extensive sample pretreatment steps including enrichment and extraction. Also, highly trained staff are required to perform the assay and analyze the results. Moreover, polymerase chain reaction (PCR) inhibitors such as humics are commonly presented in complex food matrices and must be removed prior to analysis (Shriver-lake L C et al., 2007). Other immunoassay-based methods have been recently employed to achieve lower levels of sensitivity while avoiding many of the disadvantages of the DNA-based assays.

However, these methods are less specific than DNA assays (Shriver-lake L C et al., 2007). Presently, researchers are attempting to improve the specificity of these assays through the employment of antibodies and the use of changes in optical properties such as the transmitted light, surface plasmon or acoustic waves resulting from antibody-antigen binding (Deisingh A K et al., 2004; Subramania A et al., 2006; Berkenpas E et al., 2006). Additionally, some of these assays used fluorescent labels to provide an optical signal (Nyquist-Battie C et al., 2005; Ho J A A et al., 2003). However, limitations of these assays are related to the inconsistency and high variability of target DNA labeling. In addition, they utilize expensive and nonportable scanners for data acquisition and analysis (Call D R et al., 2005; Kuck L R et al., 2008; Vora G J et al., 2008). Other alternative detection methods such as enzyme-linked immunosorbent assay (ELISA) (Abuknesha R A et al., 2005), spectrometric (Siripatrawan U et al., 2007) and electrochemical were also employed (Guo Y et al., 2015) for the detection of food borne pathogens. With these methods a detection range of $10^3$ to $10^5$ cells mL$^{-1}$ was achieved without enrichment and was as low as 1 CFUmL$^{-1}$ with enrichment. Nevertheless, this low limit of detection is valid only for the detection of microorganism that can be grown on specific media. Kuck L R et al. (2008) have illustrated a colorimetric assay for bacterial detection. This assay used unstable reagents that require temperature-controlled environments with a variable development times, leading to an increase in nonspecific background (Kuck L R et al., 2008). Notably, none of the above mentioned detection methods fully satisfy the detection performance criteria since they are sophisticated, costly in terms of both time and money and requires burdensome preparation steps.

*Porphyromonas gingivalis* (*P. gingivalis*)

Periodontal diseases are inflammatory diseases of microbial etiology affecting the hard and soft supporting tissues of the teeth (Feng Z M et al., 2006). The term "periodontal disease" encompasses two subclasses, gingivitis and periodontitis. Gingivitis is characterized by the inflammation of the gums without loss of connective tissue attachment or bone. Gingivitis is a prerequisite for, but does not necessarily lead to periodontitis (Armitage G et al., 1997; Listgarten M et al., 1980; Fowler C F et al., 1982; Kretschmar S et al., 2012) which affects approximately 7-15% of the adults in the western world, making it one of the most common diseases (Bostanci N et al., 2012). Moreover, epidemiological and mechanistic evidence has linked periodontitis to other systemic illness such as atherosclerosis, cardiovascular diseases and rheumatoid arthritis (Zhang B et al., 2013; Darveau R P et al., 2010; Kebschull M et al., 2010; Ogrendik M et al., 2013).

The microbiota of the human oral mucosa consists of a myriad of bacterial species that normally exist in commensal harmony with the host (Mysak J et al., 2014). However, studies have implicated a specific bacterial group, named as "red complex" and including *Porphyromonas gingivalis*, *Tannerella forsythia* and *Treponema denticola* as the causative agents of periodontal diseases (Haffajee A D et al, 1983).

In particular, *P. gingivalis* is an opportunistic pathogen, intensively participates in the initiation and progression of periodontal disease. It is a gram negative, assacharolytic, black-pigmented species which colonizes the subgingival region (Varghese J et al., 2013). It invades tooth supporting tissues and evade the host defense mechanisms causing periodontitis (O'Brien-Simpson N M et al., 2004). It is armed with a plethera of virulence factors such as lipopolysaccharide (LPS), gingipains, peptidyl arginine deiminase, haemagglutinins, fimbriae and outer membrane proteins (Bostanci N et al., 2012; Haffajee A D et al., 1983; Holt S C et al., 1999; Lamont R J et al., 1998; Robertson P B et al., 1982). These virulence products assist its survival in periodontal pocket and contribute to the destruction of the tooth's supportive tissues. Also, these products weaken hosts' defense system during the periods of elevated bacterial activity. Gingipains, which are typsin-like cysteine proteases account for at least 85% of the general proteolytic activity displayed by *P. gingivalis* (Kaman W E et al., 2012; Haffajee A D et al., 1983). The current understanding of periodontitis pathogenesis suggests that gingipain proteases have an important role in the disease onset and progression (Kaman W E et al., 2012).

Up to date, many methods have been developed to assess periodontal diseases. Some of these methods include subjective observational indices which are based on criteria such as bleeding on gentle probing, pocket depth, attachment loss and radiographic evidence of bone loss. Of these indicators, only bleeding on probing has been claimed to correlate with active periodontal disease. Nevertheless, bleeding itself is a subjective indicator of disease and the diagnostic value of bleeding on probing has been questioned, as such bleeding appears to be allied with a high proportion of false positive indications of periodontal disease (Haffajee A D et al., 1983). Moreover, this method does not identify the causative agents (Kaman W E et al., 2012). An alternative diagnostic methods capable of identifying the periodontal pathogens include culture-based, nucleic acid-based and antibody-based assays (Choe Y et al., 2006; Kuboniwa M et al., 2003; Jervoe-Storm P M et al., 2010). However, these methods were very laborious and time consuming. So far, direct detection and identification of periodontal pathogens in situ have proven difficult (Kaman W E et al., 2012). Furthermore, Loesche and coworkers described a diagnostic test based on the enzymatic diagnosis of periodontal pathogens (Loesche W J et al., 2010). However, these test required the use of sophisticated instrument and a trained personnel. Currently, diagnostic tests are based on the measurement of a specific component in the cervicular fluid or the measurement of cerevicular fluid volume. This was based on the fact that gingivitis and periodontitis were characterized by accumulation and flow of cervicular fluid (a transudate of serum) at the gingival sulcus and pockets.

Notably, a clear lack of biochemical markers useful for the detection of current and future periodontal disease activity in the cervicular fluid prompted researchers to look for a specific chemical compound, mainly a protein, such as an enzyme or a cytokine, in fluids from the oral cavity of a patient, such as gingival cervicular fluid (GCF) to successfully and specifically diagnose periodontal diseases (Mailhot J M et al., 1998) and ultimately aid in the design of more effective therapies.

*Listeria monocytogens* (*L. monocytogens*)

*Listeria* is a gram positive, rod-shaped, non-spore-forming facultative anaerobic bacteria consisting of six species: *L. monocytogenes, L. innocua, L. seeligeri, L. welshimeri, L. ivanovii*, and *L. grayi*. Out of which, *L. monocytogenes* species is commonly associated with human listeriosis.

Listeriosis is a disease manifested by fever and muscles ache. It could be either in an invasive or noninvasive form. The invasive form can spread to the central nerves system causing headache, stiff neck, and confusion, loss of balance, convulsion and ocular listeriosis (Mead P S et al., 2006). Also, listeriosis is highly common among pregnant women (Centers for Disease Control and Prevention, 2013), elderly patient above 65 year (CDC, 2011) and in immunocompromised patients (Bala B, 2007). In pregnant women listeriosis causes miscarriage, stillbirth, perinatal septicemia and meningitis in new born baby (Mokta et al., 2010).

As an issue of concern, *L. monocytogenes* is considered a major source of human foodborne illness worldwide due to its presence in the ready to eat food (Roberts T et al., 2009; Vazquez-Boland J A et al., 2001; Garrido V et al., 2008; O'Connor L et al., 2010; Junttila J R et al., 1988; Liu D, 2006). At present, the United States Department of Food Safety and Inspection Services (FSIS) spent billions of dollars for inspection of bacterial contamination annually (Centers for Disease Control and Prevention, 2013). *Listeria* has been widely observed in environmental samples such as water, soil, silage and in food samples such as dairy product (milk, soft cheese), meat, and sea food (cooked and raw). This microbial contaminant can tolerate high environmental stress form and a wide range of temperature ($-18$ to $10°$ C.), being a psychrophillic organism.

In food industry the time between food packaging, inspection and consumption is crucial as small undetectable number of microbes at the time of packing can multiply and become life threatening by the time of consumption. However, *L. monocytogenes* detection in foods is hampered by certain limitation as the high population of competitive microflora, the low levels of the pathogen and the interference of inhibitory food components (Norton D M, 2002).

Typically, *L. monocytogenes* detection and identification in food involve standard culturing technique which requires trained personnel and long time as negative results can be confirmed in 3-4 days. Whereas, positive results might take 5-7 days (Jadhav S et al., 2012; Alessandria V et al., 2010; Kabuki D Y et al., 2004; Frece J et al., 2010; Gasanov U et al., 2005; Brehm-Stecher B F et al., 2007). Notably, in food industry, it is not common to hold food products for 7 days prior to distribution. Moreover, the standard culture method requiring selective enrichment with subsequent culturing on selective media, followed by serological and/or biochemical tests (Wang D et al., 2011). Later on, alternativether method based on specific antigen-antibody reaction was developed, but this immuno assay method was less sensitive than culturing method with a lower limit of detection (LOD) of $10\pi$-$10\upsilon$ cells/ml (Gasanov U et al., 2005). Moreover, antibody preparation is time consuming with a chance of detecting false positive (Zhang D et al., 2009). Other method based on nanoparticle immuno magnetic separation and real-time Polymerase Chain Reaction (PCR) was able to de lect $10^2$ CFU/0.5 mL of *L. monocytogens* in milk (Yang H et al., 2007). However, this method is limited by the presence of PCR inhibitors in the real biological samples and food samples. Therefore, it is necessary to develop a rapid, sensitive, and cost-effective method for microbiological examination of real food samples.

*Listeria* has several virulence factor which contributes to its pathogenicity. During the infection, *L. monocytogenes* invade the host cell by lysing the phagocytic vacuoles and proliferate in the cytosol with the help of Listeriolysin O (LLO) and two secreted phospholipases C (PLC): a broad-range phospholipase C (PC-PLC) and a phosphatidylinositol specific PLC (PI-PLC) (Portnoy D A et al., 1992; Smith G A et al., 1995). Broad-range phospholipase C is released in an inactive propeptide and it is activated by the cleavage of the propeptide by a metalloprotease (Mpl) at low pH. 15. Accordingly, higher level of zinc dependent-metallo pro- tease would be observed in the host infected with *L. monocytogens*. This virulence protease capable of cleaving specific substrate (Mitchell C S et al., 2003; Kasana R C et al., 2011) could be used as a biomarker for the detection of *L. monocytogens* food contamination. Remarkably, Mitchell C S et al. (2003), pronounced a specific peptide substrate which could be selectively cleaved by *L. monocytogens* protease.

Accordingly, there is still a need to develop simple, sensitive, specific, rapid, cost-effective colorimetric bio sensors capable of detecting the presence or absence of a pathogenic microorganism in a sample upon suspicion. The sample may be related to food products, hospitals, health centers or any other environment.

SUMMARY

The present disclosure is drawn to a biosensor for detecting pathogens in a sample. The detection is based on colorimetry. The biosensor comprises one or more particle supports and a magnetic material attached to a planar support. The biosensor embodies magnetic particles that are functionalized using a chemical substrate specific to the pathogens to be detected. The sensor of this disclosure may allow for a simultaneous detection of a plurality of pathogens in the sample. Also, the sensor of this disclosure may be disposable. Moreover, the sensor may be integrated in a portable detection device. The pathogen may be selected from the group consisting of *Pseudomonas aeruginosa, Staphyloccocus aureus, Escherichia coli, Porphyromonas gingivalis* and *Listeria monocytogens*. A sample analyzed using the sensor of this disclosure may be of various origins. For example, the sample may be of biological origin, of clinical origin, from a patient; from food, from a chemical plant, from an industrial plant, from a hospital, from a school or from the environment.

Several embodiments for the sensor and method of use of this disclosure are outlined below.

According to an aspect, this disclosure relates to a biosensor for detecting a pathogen in a sample, comprising: a planar support; a particle support attached to a surface of the planar support, the particle support being of a first color; a magnetic material attached to the other surface of the planar support and spaced apart from the location of the particle support; and a plurality of magnetic particles of a second color different from the first color, each particle being attached to the particle support through a chemical substrate specific to the pathogen to be detected, a first end of the chemical substrate being attached to the magnetic particle and a second end of the chemical substrate being attached to particle support, such that a visual inspection of the particle support reveals only the second color, the first color being masked by the magnetic particles, wherein upon contacting the particle support with the sample, a reaction occurs between the chemical substrate and the pathogen which results in the magnetic particle being released from the particle support revealing the second color, and the released magnetic particle is attracted by the magnetic material.

In one embodiment, the magnetic particles are nanoparticles.

In one embodiment, the planar support is of plastic material, or is dielectric, or is a piece of paper, or is a piece of cloth.

In one embodiment, the particle support is of metal material, or of plastic material, or is dielectric, or is a piece of paper, or is a piece of cloth.

In one embodiment, the sensor comprises two or more particle supports.

In one embodiment, the chemical substrate is a peptide substrate that may be cleaved by the pathogen.

In one embodiment, the sensor further comprises a first linker between the first end of the chemical substrate and the magnetic particle and a second linked between the second end of the chemical substrate and the particle support, the first and second linkers being the same or different.

In one embodiment, the sensor comprises two or more particle supports, of the same color or of different colors.

In one embodiment, the sensor comprises first and second particle supports, wherein a first set of magnetic particles attached to the first particle support is of a color, and a second set of magnetic particles attached to the second particle support is of another color.

In one embodiment, the sensor comprises first and second particle supports, wherein a first chemical substrate attached to the first particle support is specific to a pathogen, and a second chemical substrate attached to the second particle support is specific to another pathogen.

In one embodiment, the pathogen is selected from the group consisting of *Pseudomonas aeruginosa, Staphyloccocus aureus, Escherichia coli, Porphyromonas gingivalis* and *Listeria monocytogens*.

In one embodiment, the sample is of biological origin, of clinical origin, from a patient, from food, from a chemical plant, from an industrial plant, from a hospital, from a school or from the environment.

In one embodiment, the sensor is disposable.

According to another aspect, this disclosure relates to a biosensor for detecting a pathogen in a sample, comprising: a planar support; a golden strip attached to a surface of the planar support; a magnetic material attached to the other surface of the planar support and spaced apart from the location of the golden strip; and a plurality of colored magnetic nanoparticles, each particle being attached to the golden strip through a chemical substrate specific to the pathogen to be detected, a first end of the chemical substrate being attached to the colored magnetic nanoparticle and a second end of the chemical substrate being attached to golden strip, such that a visual inspection of the golden strip reveals only the color of the nanoparticles, wherein upon contacting the golden strip with the sample, a reaction occurs between the chemical substrate and the pathogen which results in the colored magnetic nanoparticle being released from the golden strip revealing the golden color, and the released colored magnetic particle is attracted by the magnetic material.

According to a further aspect, this disclosure relates to a method of detecting a pathogen in a sample, comprising: (a) providing a planar support comprising a particle support of a first color attached to a surface thereof and a magnetic material attached to the other surface thereof spaced apart from the location of the particle support; (b) providing a plurality of magnetic particles of a second color different from the first color; (c) providing a chemical substrate specific to the pathogen to be detected, the chemical substrate having first and second ends; (d) attaching the first end of the chemical substrate to the magnetic particles to obtain functionalized magnetic particles; (e) attaching the functionalized magnetic particles to the particle support through the second end of chemical substrate to obtain a functionalized particle support, such that a visual inspection of the functionalized particle support reveals only the second color, the first color being masked by the functionalized magnetic particles; and (f) contacting the functionalized metal strip with the sample, wherein, if the pathogen is present in the sample, a reaction occurs between the chemical substrate and the pathogen which results in the magnetic particle being released from the metal strip revealing the second color, and the released magnetic particle is attracted by the magnetic material, and if the pathogen is absent, no reaction occurs and no color change is observed.

In one embodiment, the method further comprises a washing step after step (d) to remove any unattached chemical substrate.

In one embodiment, the method further comprises, after step (e), a step of passing a magnet above the particle support to remove any unattached functionalized magnetic carrier.

In one embodiment, step (f) comprises dropping the sample on the functionalized particle support, or swabbing the sample with the functionalized particle support, or delivering the sample on to the functionalized particle support by capillary action or use of a micro-fluid.

Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which:

FIG. 1 Outline of the pathogen detection method of this disclosure.

FIGS. 4A-4N Isolates from patient samples.

FIGS. 6A-6J Colorimetric *S. aureus* sensor probe application on spiked food produces (specific *S. aureus* substrate peptide covalently bound to a magnetic bead). (FIG. 6A, FIG. 6C, FIG. 6E, FIG. 6G and FIG. 6I) Biosensor chip functionalized with magnetic beads-specific *S. aureus* peptide substrate. (FIG. 6B, FIG. 6D, FIG. 6F, FIG. 6H and FIG. 6J) Functionalized biosensor under the effect of different *E. coli* protease concentrations spiked in food produces.

FIGS. 7A-7H Colorimetric *S. aureus* sensor probe application on spiked environmental samples (specific *S. aureus* substrate peptide covalently bound to a magnetic bead). Visual comparison of the golden color of the exposed probe to negative control (unspiked food produces, A, B and C) and spiked samples: I before application of negative control, II after application of negative control. FIG. 7C, FIG. 7E and FIG. 7G for different food produces before application and FIG. 7D, FIG. 7F and FIG. 7H after application.

(FIG. 9A and FIG. 9C) Biosensor chip functionalized with magnetic beads-specific *S. aureus* peptide substrate. (FIG. 9B and FIG. 9D) Functionalized biosensor under the effect of *Listeria* and *Pseudomonas* proteases.

(FIG. 10A) Biosensor chip functionalized with magnetic beads-specific *E. coli* peptide substrate. (FIG. 10B) Functionalized biosensor under the effect of different *E. coli* protease concentrations.

(FIG. 11A) Biosensor chip functionalized with magnetic beads-specific *E. coli* peptide substrate. (FIG. 11B) Functionalized biosensor incubated with different proteases. (FIG. 11C) Functionalized biosensor after the incubation with different proteases.

FIGS. 12A-12H Colorimetric *E. coli* sensor probe application on spiked food produces (specific *E. coli* substrate peptide covalently bound to a magnetic bead). (FIG. 12A, FIG. 12C, FIG. 12E and FIG. 12G) Biosensor chip functionalized with magnetic beads-specific *E. coli* peptide substrate. (FIG. 12B, FIG. 12D, FIG. 12F and FIG. 12H) Functionalized biosensor under the effect of different *E. coli* protease concentrations spiked in food produces.

(FIG. 15A) Examination of healthy control saliva (negative result). (FIG. 15B) Examination of periodontitis patients' saliva (positive result).

Figure 2A:
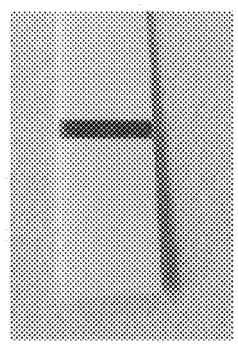
FIGS. 2A-2B Colorimetric *Pseudomonas aeruginosa* sensor probe tested with blank.

Other features of the present embodiments will be apparent from the accompanying drawings and from the detailed description that follows.

DETAILED DESCRIPTION

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

The use of the word "a" or "an" when used in conjunction with the term "comprising" in the claims and/or the description may mean "one", but it is also consistent with the meaning of "one or more", "at least one", and "one or more than one". Similarly, the word "another" may mean at least a second or more.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The present disclosure is drawn to a biosensor for detecting pathogens in a sample. The detection is based on colorimetry. The biosensor comprises one or more particle supports and a magnetic material attached to a planar support. The biosensor embodies magnetic particles that are functionalized using a chemical substrate specific to the pathogens to be detected. The sensor of this disclosure may allow for a simultaneous detection of a plurality of pathogens in the sample. Also, the sensor of this disclosure may be disposable. Moreover, the sensor may be integrated in a portable detection device. The pathogen may be selected from the group consisting of *Pseudomonas aeruginosa, Staphyloccocus aureus, Escherichia coli, Porphyromonas gingivalis* and *Listeria monocytogens*. A sample analyzed using the sensor of this disclosure may be of various origins. For example, the sample may be of biological origin, of clinical origin, from a patient; from food, from a chemical plant, from an industrial plant, from a hospital, from a school or from the environment.

The pathogen detection method of this disclosure is outlined in FIG. 1. A biosensor which is a planar support 10 comprises a particle support or golden strip 12 (on the upper surface) and the magnetic material or permanent magnet 14 (on the lower surface). A functionalized nanoparticle 16 comprises a black nanoparticle 18 having a chemical substrate 20 attached thereto. The first step in FIG. 1 illustrates attachment of functionalized nanoparticles 16 to the particle support or golden strip 12 to obtain a functionalized golden strip 22. The functionalized magnetic nanoparticles are assembled on the whole surface of the golden strip in a mono layer such that the only the black color is visible to the eyes, the golden color being masked by the nanoparticles. The second step in FIG. 1 illustrates the reaction between the analyte 22 with the chemical substrate 20. This leads to the cleavage of the link between the magnetic nanoparticles and the particle support or golden strip 12, thus revealing the golden color. A magnetic nanoparticle released 26 comprises part of the chemical substrate and also part of the chemical substrate 28 remains on the golden strip. Some functionalized magnetic nanoparticles 30 may remain on the golden strip.

As will be understood by a skilled person, the planar support 10 may be of plastic material, or is dielectric, or is a piece of paper, or is a piece of cloth. Also as will be understood by a skilled person, the particle support 12 may be of metal material, or of plastic material, or is dielectric, or is a piece of paper, or is a piece of cloth.

The analyte or sample may be brought into contact with the functionalized particle support or functionalized golden strip in various ways. This may involve dropping the sample on the functionalized particle support, or swabbing the sample with the functionalized particle support, or delivering the sample on to the functionalized particle support by capillary action or use of a micro-fluid; or other suitable way known to s skilled person.

Description of a Preferred Embodiment in Relation to a *Pseudomonas aeruginosa* (*P. aeruginosa*) Protease Materials and Reagents Carboxyl-terminated beads (50 nm diameter) were provided by Turbo beads (Switzerland) via Sigma Aldrich (Dorset, UK). N-Hydroxysuccinimide (NHS), 1-(3-dimethylaminopropyl)-3-ethyl-carbodiimide (EDC) and the plastic pH indicator strip were purchased from Sigma Aldrich (Amman, Jordan). Self-adhesive Magnet sheets were purchased from Polarity Magnets Company (UK). The peptide sequence (Seq Id #1) $NH_2$-Ahx-Gly-Gly-Gly-Ahx-Cys was synthesised by Pepmic Co., Ltd. (Suzhou, China). The self-adhesive tape was purchased from Whatman (London, U.K). Brain Heart Infusion broth (BHI) and agar were purchased from (SDA, Oxoid, Ltd., Basingstoke, UK). Sterile filter 0.22 µm from Millipore (Amman, Jordan). The wash/storage buffer (10 mM tris base, 0.15 M sodium chloride, 0.1% (w/v) bovine serum albumin, 1 mM ethylenediaminetetraacetic acid, 0.1% sodium azide, pH 7.5), the coupling buffer (10 mM potassium phosphate, 0.15 M sodium chloride, pH 5.5) were prepared from chemicals of analytical grade.

Bacterial Strain Culturing

*Pseudomonas aeruginosa* (ATCC 15692 PAO1), *Staphylococcus aureus* (ATCC25923), *Listeria monocytogenes* (ATCC 19115) were streaked on BHI agar plate and incubated at 37° C. for 24 hours. One colony was then isolated inoculated into BHI broth and incubated overnight at 37° C. The primary bacterial culture (PBC) was then serially diluted and surface plated on the BHI agar plat. After 24-h incubation at 37° C., concentrations of the all bacteria were enumerated. The inoculum of *Pseudomonas aeruginosa* was diluted serially and was saved for subsequent experiments.

Conjugation of the *P. gingivalis* Substrate Peptide to Magnetic Bead

Magnetic bead suspension (1 ml) was mixed with the peptide (1.0 mg/mL), coupling agent EDC (0.57 mg/mL) and NHS (12 µg/mL). The mixture was tremor gently at room temperature for 24 hours. The uncoupled peptides were removed by washing the beads 3 times using wash buffer. Finally, the beads were stored at 4° C. in a storage buffer.

Gold Sensor Platform Preparation

Self-adhesive sheet was purchased from Whatman (London, UK) and gold plated at canfield university engineering department. The sheet was cut into small stripes and stacked over a plastic strip at standardized distance. This plastic strip was used as a physical support for the whole biofunctionalization process as well as *P. gingivalis* protease detection and quantification sensor.

Sensing Monolayer and Probe Immobilization

Figure 2B:
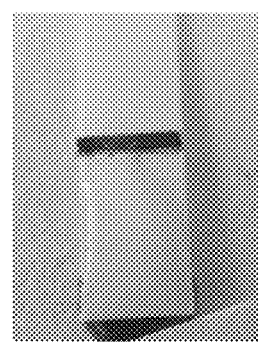

The gold sensing surface was covered with the magnetic bead-peptide solution and allowed to stand at room temperature 30 minutes (step 1 in FIG. 1). After which, an external magnet (12.5×12.5×5 mm) with field strength of 3360 gauss and 573 gauss at 1 mm and 10 mm distance, respectively was passed over the functionalized strip from a distance of 3 to 5 mm to remove any unattached magnetic beads. Round permanent paper magnet was fixed on the strip back, 2-3 mm distance below the gold sensor platform as shown in FIGS. 2A-2B.

Biosensing of *Pseudomonas aeruginosa* Proteases

Figure 3:
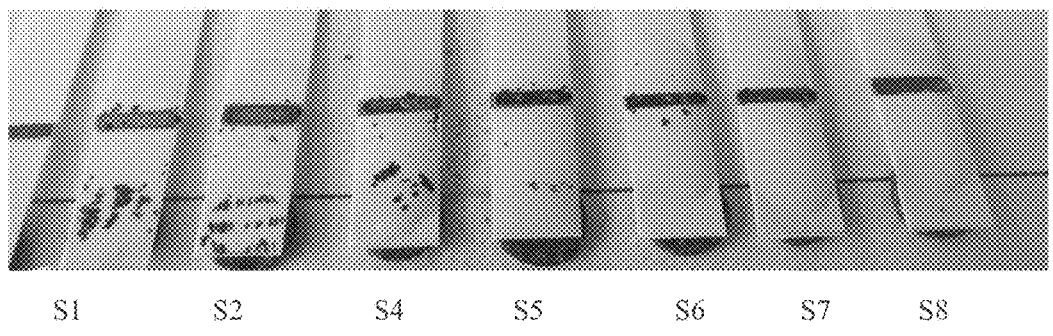
FIG. 3 Colorimetric *Pseudomonas aeruginosa* sensor probe (specific *Pseudomonas aeruginosa* substrate peptide covalently bound to a magnetic beads) under the effect of different concentration starting from the highest concentration S1 ($4.5 \times 10^8$ CFU/M1).

*P. aeruginosa* proteases solution was down streamed over the functionalized sensor platform. During the enzymatic cleavage reaction, the permanent magnets will attract the released magnetic beads prompting a visual observation for a qualitative evaluation of the tested samples (step 2 in FIG. 1). Moreover, a powerful quantitative evaluation was possible by using different concentrations of *P. gingivalis* proteases solution ($4.5 \times 10^8$ CFU/mL, $4.5 \times 10^7$ CFU/mL, $4.5 \times 10^6$ CFU/mL, $4.5 \times 10^5$ CFU/mL, $4.5 \times 10^4$ CFU/mL, $4.5 \times 10^3$ CFU/mL, $4.5 \times 10^2$ CFU/mL, 45 CFU/mL, 4.5 CFU/mL) as shown in FIG. 3.

Saliva Collection and Spiking

Saliva was collected from one volunteer with no history of periodontal diseases under consistent conditions from 7:00 in the morning to the lunch time, with no eating and or smoking for 2 hours prior to collection. Saliva was then stored at −20° C. for later use. Spiking with *P. aeruginosa* proteases (50 μl of saliva and 20 μl of various *P. gingivitis* proteases concentrations) was before application on the disposable sensor. Saliva sample was also spiked with culture broth as a negative control. FIGS. 4A-4N show isolates from patient samples.

Description of a Preferred Embodiment in Relation to a *Staphyloccocus aureus* Protease Materials and Reagents Carboxyl-terminated beads (50 nm diameter) were provided by Turbo beads (Switzerland) via Sigma Aldrich (Dorset, UK). N-Hydroxysuccinimide (NHS), 1-(3-dimethylaminopropyl)-3-ethyl-carbodiimide (EDC), plastic pH indicator strips were purchased from Sigma Aldrich (Amman, Jordan). Self-adhesive magnet sheets were purchased from Polarity Magnets Company (UK). The peptide sequence (Seq Id #2) $NH_2$-Ahx-ETKVEENEAIQK-Ahx-Cys was synthesised by Pepmic Co., Ltd. (Suzhou, China). The self-adhesive tape was purchased from Whatman (London, UK). Brain Heart Infusion broth and agar were purchased from (SDA, Oxoid, Ltd., Basingstoke, UK). Sterile filter 0.22 μm was from Millipore (Amman, Jordan). The wash/storage buffer (10 mM tris base, 0.15 M sodium chloride, 0.1% (w/v) bovine serum albumin, 1 mM ethylenediaminetetraacetic acid, 0.1% sodium azide, pH 7.5), the coupling buffer (10 mM potassium phosphate, 0.15 M sodium chloride, pH 5.5) were prepared from chemicals of analytical grade.

Conjugation of the Peptide Substrates to Magnetic Bead

Magnetic bead suspension (1 ml) was mixed with the peptide at a concentration of (1.0 mg/mL), coupling agent EDC (0.57 mg/mL) and NHS (12 μg/mL). The mixture was tremor gently at room temperature for 24 hours. The uncoupled peptides were removed by washing the beads 3 times using wash buffer. Finally, the beads were stored at 4° C. in a storage buffer (Suaifan G A et al., 2012; Suaifan G A et al., 2013; Esseghaier G A et al., 2014).

Gold Sensor Platform Preparation

Whatman self-adhesive tape was coated with a thin layer (30 nm) of gold. After which, a rectangular stripe (~1.5-2×3 mm) was stacked over the sensor platform. This strip acted as a physical support for the whole bio-functionalization process as well as the bacterial protease detection and quantification sensor (Suaifan G A et al., 2012; Suaifan G A et al., 2013; Esseghaier G A et al., 2014).

Sensing Monolayer and Probe Immobilization

Magnetic bead-peptide solution was topped over the gold sensing surface and allowed to dry at room temperature. Afterward, an external magnet (12.5×12.5×5 mm) with a field-strength of 573 gauss at a distance of 10 mm was passed over the functionalized strip to remove any unattached magnetic beads. Around paper magnet was fixed on the back of the strip, at 5 mm below the gold sensor platform as shown in FIG. 1 (Suaifan G A et al., 2012; Suaifan G A et al., 2013; Esseghaier G A et al., 2014).

Bacterial Strain Culturing

*S. aureus* (ATCC 25923), *Listeria monocytogenes* (ATCC 19115), and *Pseudomonas aeruginosa* (*P. aeruginosa*, ATCC 15692) were streaked on BHI agar plate and incubated at 37.0° C. for 24 hours. One colony was then isolated, inoculated into BHI broth and incubated overnight at 37° C. The primary bacterial culture (PBC) was then serially diluted and surface plated on the BHI agar plate. After 24-hours incubation at 37.0° C., concentrations of all bacteria were enumerated. The inoculum of *S. aureus* was diluted serially and was saved for subsequent experiments.

Bacterial Spiking and Roteases Preparation

Food Products

Food products (ground beef, turkey sausage, lettuce and milk) were purchased from a local market in Amman-Jordan. Ground beef and turkey sausage were homogenized with sterile water at 1:5 (w:v) ratio in a blender for 1 minute and then were rocked at room temperature for 2 hours. Lettuce leaves were rinsed with vegetable detergent and phosphate buffered saline (PBS; pH 7.4) and then cut into 4-cm² pieces using sterile scissors to remove any potential adulterates which may exist on the leafy surface.

Afterward, the PBC stock of *S. aureus* was spiked into these food products to create a 10-fold dilution samples. The spiked matrices were allowed to incubate at room temperature for 2 hours and then clarified by centrifugation (5 minutes, 2000 rpm) (Medina M B et al., 2003). The supernatant was then collected, centrifuged (10 minutes, 3000×g) to concentrate bacteria and then filtered through a 0.22 μm sterile filter. The crude sample's filtrate containing the bacterial secreted proteases were either used immediately or stored at −20° C. for later use. Positive control was prepared by creating 10-fold dilution from the *S. aureus* PBC stock. The number of bacteria was determined by plating 10-fold serial dilutions of the positive control (PBC) on the BHI agar plates. The plates were then incubated at 37° C. overnight and then bacteria were enumerated.

Environmental Samples

Dust samples were wiped from different places (Hospital Intensive Care Unit, Hospital stairs and The University of Jordan courtyard corners) and suspended in sterile water. Afterward, different *S. aureus* PBC dilution were spiked into the dust samples and kept at room temperature for about 2 hours. The samples were then clarified by centrifugation at 3000×g for 10 minutes and the supernatant was filtered through a 0.22 μm sterile filter. The filtrates were either used immediately or stored at −20° C. for later use. Unspiked dust samples were used as a negative control.

Clinical Biosamples

Clinically Isolated Pathogens

Five clinical isolates (*S. aureus, P. aeruginosa* brown and green, *E. coli* and *Candida albicans* were obtained from The University of Jordan hospital. These isolates were identified and characterized by the mycological investigation laboratory at the hospital and provided as an inocula in the proper broth with 5% glycerol and then was stored at −20° C. for later use.

Biosensing of *S. aureus* Proteases

Figure 5A:
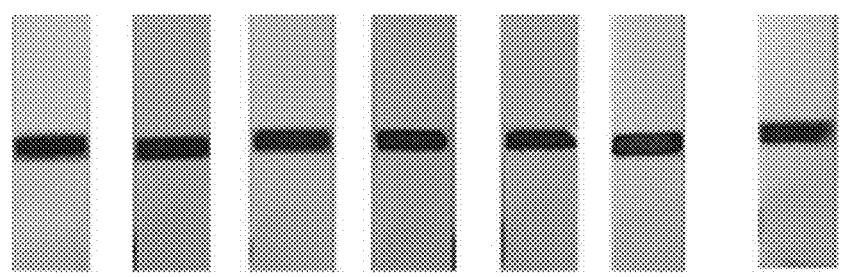
FIGS. 5A-5B Colorimetric *Staphylococcus aureus* sensor probe (specific *Staphylococcus aureus* substrate peptide covalently bound to a magnetic bead) under the effect of different *Staphylococcus aureus* protease concentrations.
Figure 5B:
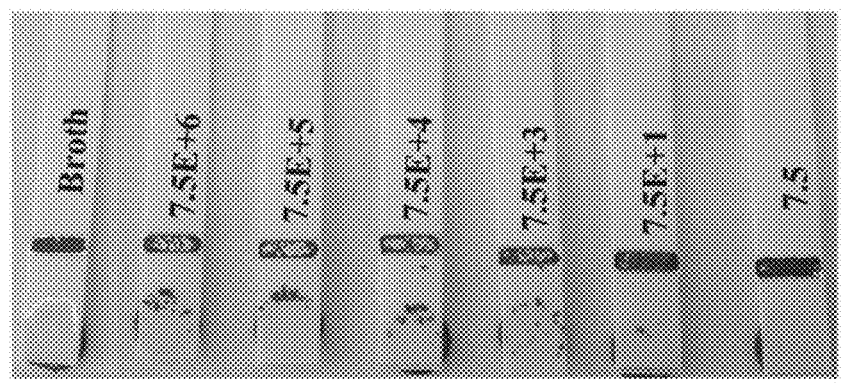

*S. aureus* protease solution was loaded over the functionalized sensor platform. During the enzymatic cleavage reaction, the permanent magnets will attract the released magnetic beads prompting a visual observation for a qualitative evaluation of the tested samples (FIG. 1). Moreover, a powerful quantitative evaluation was possible by using different concentrations of *S. aureus* protease solutions ($7.5 \times 10^6$ CFU/mL, $7.5 \times 10^5$ CFU/mL, $5 \times 10^4$ CFU/mL, $5 \times 10^3$ CFU/mL, $5 \times 10^2$ CFU/mL, 75 CFU/mL, 7.5 CFU/mL) as shown in FIGS. 5A-5B.

Results and Discussion

Accordingly, despite the attractiveness of various diagnostic techniques applied to date, there are still some potential shortcomings in adapting these techniques for point-of-care (POC) testing. At the present time, nanotechnology advances in the field of biosensors have resulted in a broad range of biosensing application. Colorimetric biosensors are attracting due to their simplicity and low cost. These biosensors are convenient because of the ease in qualitative detection by eyes without the need for a specific apparatus. However, quantitative detection of the color change is usually accomplished by using instruments as spectrophotometer, epifluorescence microscope and luminescence counter.

Notably, colorimetric disposable biosensors which identify bacterial specific proteins, such as proteases which can act as a specific marker for that microbe would provide a diagnostic tool (Hanumegowda N M et al., 2005; Zhou Y et al., 2007). Therefore, in this disclosure we investigated the strength of implementing nanotechnology science within the field of biosensors for specific *S. aureus* detection in a variety of fields.

Sensor Fabrication

The designed colorimetric biosensor comprises a specific protease substrate coupled with a carboxy terminated nano magnetic beads. These beads have a large surface to volume ratio which induces efficient interaction with the target even in a dilute sample (Citartan M et al., 2012). Also, it may be covalently bound to the gold sensor surface. Upon proteolysis of the substrate-magnetic beads, a colorimetric visual readout by naked eyes would point out the presence of *S. aureus* as described in FIG. 1. A specific peptide substrate (Seq Id #3) (ETKVEENEAIQK) (Sanders M C et al., 2005) was used in order to specifically detect the activities of *S. aureus* proteases and so the biosensor could be considered as a promising diagnostic biomarker. The biosensor consists of a peptide probe which is prepared by using *S. aureus* specific substrate elongated with Ahx-residue linker on either termini of the peptide ($NH_2$-Ahx-ETKVEENEAIQK-Ahx-Cys). The N-terminal of the peptide was attached to the magnetic bead. The cysteine residue at the C-terminal, will allow covalent interaction with the gold-sulfur to establish a self-assembled monolayer (SAM) of peptide and magnetic bead on the surface of the gold sensor (Suaifan G A et al., 2012; Esseghaier C et al., 2014; Suaifan G A et al., 2013). Usually, the optimum amount of substrate depends upon its molecular weight (MW) and its relative affinity for the beads as well as the surface area of the beads (Cantarero L A et al., 1980).

Magnetic beads-peptide solution was mounted over the gold surface and allowed to dry at room temperature to ensure proper functionalization. After which, the golden color of the gold strip changed to black as a result of complete immobilization. Afterward, an external magnetic field was passed over the functionalized gold sensor to remove any non-immobilized functionalized magnetic bead. The sensor was then ready for *S. aureus* protease detection as shown in FIG. 1.

Sensor Testing

The proteolytic activity of *S. aureus* protease was analyzed by dripping 30 µL, of protease solution ($7.5 \times 10^6$ CFU/mL) over the functionalized gold sensor. An external magnet was fixed on the back of the sensor to accelerate the cleavage of the peptide-magnetic bead moiety from the sensor surface. The dissociation process of the black peptide-magnetic bead moiety from the sensor surface followed by attraction of the beads towards the permanent magnet thus revealing the golden color of the sensor surface visible to the naked eyes as shown in FIG. 1.

To quantitatively determine the amount of *S. aureus* protease, different concentration of *S. aureus* protease solutions were dripped over the functionalized sensor ($7.5 \times 10^6$ CFU/mL, $7.5 \times 10^5$ CFU/mL, $5 \times 10^4$ CFU/mL, $5 \times 10^3$ CFU/mL, $5 \times 10^2$ CFU/mL, 75 CFU/mL, 7.5 CFU/mL). A gradual increase in the visible bare gold area was directly proportional with protease solution concentration. This is due to the proteolytic activity of the protease which resulted in the dissociation of the peptide-magnetic beads complex Interestingly, the developed sensor revealed a very low level of detection (7.5 CFU/mL) without the use of any instrument and with an extraordinary short detection time of 30 seconds. Previously, limited numbers of colorimetric detection methods were developed (Tote K et al., 2008; Sung Y J et al., 2013; dos Santos Pires A C et al., 2011). However, these methods do not fully satisfy the detection performance criteria as they are sophisticated and involve burdensome preparation steps. For example, Sung et al. (2013) designed a colorimetric detection method based on the use of new antibody/gold nanoparticle/magnetic nanoparticle nano composites (anti-body/AuNP/MNPs). The detection limits were $1.5 \times 10^3$ and $1.5 \times 10^5$ CFU in Phosphate buffer saline (PBS) and milk sample, respectively. This assay required 40 minutes to obtain the results. Also, dos Santos Pires A C et al. (2011) reported the use 10,12-pentacosadyinoic acid (PCDA)+N-[(2-tetradecanamide)-ethy]ribonamide (TDER) vesicles to determine the colorimetric response induced by *S. aureus* in a culture medium and in apple juice. Alternative colorimetric methods for some food-borne pathogens used antibody-labeled gold nanoparticles (AuNPs) as an immunological reporter for an easy visual sensing of the biomolecules (Kim Y T et al., 2012; Jian J W et al., 2011; Li X X et al., 2009). However, test samples had to be purified and concentrated prior to the immunological reaction to achieve a specific and sensitive response with low noise (Li X X et al., 2009).

Biosensor Detection of *S. auerus* in Spiked Food Matrices and Environmental Samples Since we have now proved that the developed colorimetric biosensor was able to detect *S. aureus*, we next determined its feasibility to detect *S. aureus* in spiked food products and environmental samples. To contaminate food produces, fresh PBC was spiked into ground beef, turkey sausage, lettuce and milk. We first spiked 9 mL of different food product with 1.0 mL of different *S. aureus* PBC concentrations, range from $4.14\times10^5$ CFU/mL to 4.14 CFU/mL as shown in FIGS. 5A-5B. A positive control was also prepared by spiking 9 mL of water with 1 mL of PBC. A negative control was prepared by spiking 9 mL of food samples with 1 mL of BHI broth. On the other hand, to contaminate environmental samples, dust sample was suspended in sterile water and spiked with six different concentrations ranging from $1.12\times10^7$ CFU/mL to 11.2 CFU/mL as shown in FIGS. 5A-5B. Positive and negative controls were also prepared. Both the controls and the spiked samples of food products and environmental samples were allowed to incubate at room temperature for 2 hours. The samples were then centrifuged, filtered and examined on the developed biosensor. Clearly, a steady increase of the visible bare gold area in correlation with concentration was observed. The developed biosensor displayed the ability to detect *S. aureus* spiked in different food matrices and environmental samples with a low detection limit of 4 CFU/mL and 11.1 CFU/mL, respectively, in less than one minute as shown in FIGS. 6A-6J and FIGS. 7A-7H. To the best of our knowledge and accessibility to literature resources the lowest limit of detection for *S. aureus* in spiked food samples by colorimetric method was $1.5\times10^5$ CFU (Sung Y J et al., 2013). Interestingly, our biosensor approved the highest sensitivity for the detection of *S. aureus*.

Biosensor Detection of Clinically Isolated and Standard Pathogens Proteases

Figure 8A:
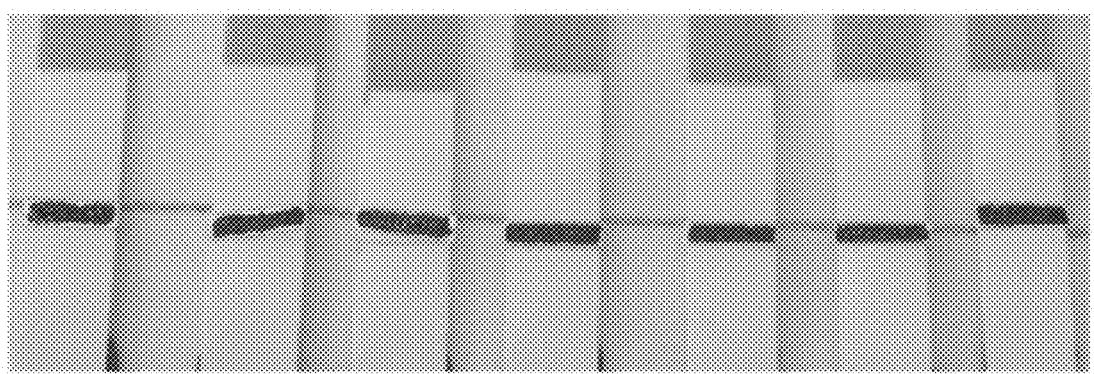
FIGS. 8A-8B Colorimetric *S. aureus* sensor probe application on different clinical isolates.
Figure 8B:
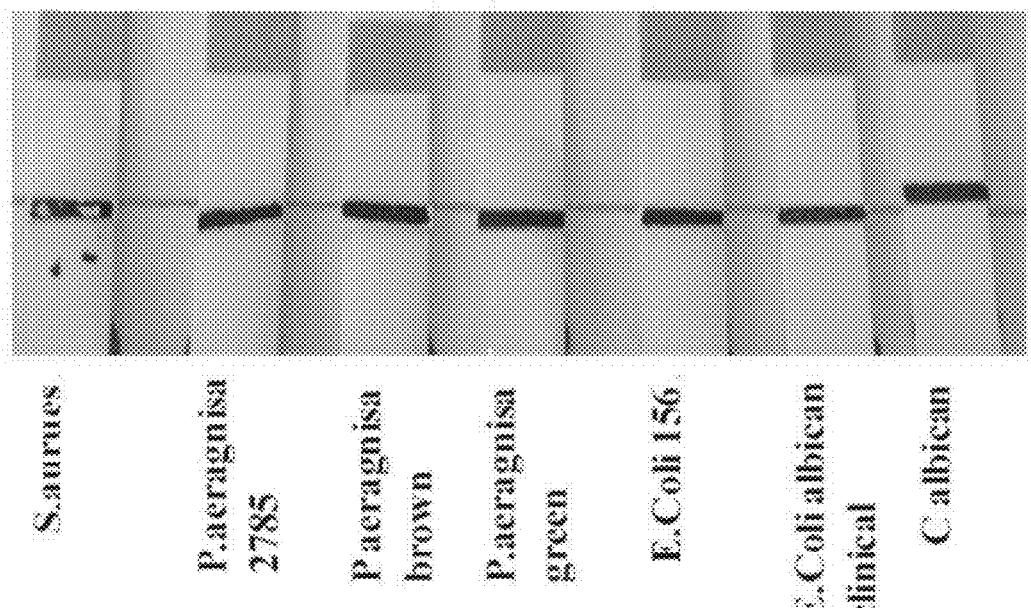
Figure 9A:
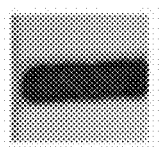
FIGS. 9A-9B Application of the colorimetric detection methods.
Figure 9B:
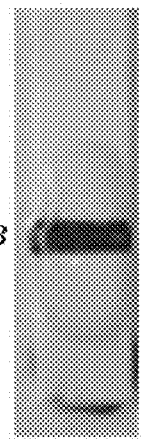
Figure 9C:
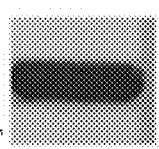
Figure 9D:
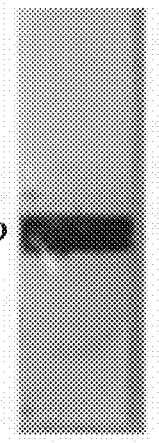

A significant improvement in disease control could be made if the target pathogen in the clinical bio-samples and food produces was specifically detected by a rapid and sensitive diagnostic assay. Thus, the specificity of the biosensor was verified initially by the application of characterized clinically isolates of infectious microorganisms (*S. aureus, P. aeraginosa* brown and green, *E. coli* and *Candida albicans*) and standard ATCC pathogens (*P. aeraginosa* 2785 and *E. coli* 156) as shown in FIGS. 8A-8B. Secondly by the use of other food contaminating microbial proteases of such as *Listeria* proteases and *P. auregenosa* protease prepared previously as shown in FIGS. 9A-9B. The sensor showed no disruption of the SAM layer for all the tested microbial pathogens and no significant change in the sensor surface golden color, except for *S. aureus*, showing high detection specificity.

As will be understood by a skilled person, this disclosure outlines the development of a biosensor to detect *S. aureus* pathogen. The biosensor is specific and may simultaneously detect *S. aureus* in complex food matrices, environmental samples and clinically isolated pathogens. The limit of detection was less than 12 CFU/mL in all of the tested targets with a positive result for *S. aureus* clinical isolates. This assay is simple to perform, rapid, requires no sample pretreatment or pre-concentration and may be performed at the retail to prevent the consumer from being susceptible to food-borne diseases or at the hospital to protect patients from hospital acquired infections. The detection method does not require any labeling or amplification schemes. It may be undertaken by anyone without the requirement of complex, sophisticated and expensive instrumentation. The method of this disclosure allows for the detection of *S. aureus* pathogen in less than a minute and with a low detection limit. The biosensor of this disclosure presents a valuable tool not only for produce industry but also for agencies to better control potential risks associated with hospital infections.

Description of a Preferred Embodiment in Relation to an *Escherichia coli* Protease Material and Reagents Carboxyl-terminated beads (50 nm diameter), N-hydroxysuccinimide (NHS), 1-(3-dimethylaminopropyl)-3-ethyl-carbodiimide (EDC) and a plastic pH indicator stripes were purchased from Sigma Aldrich (Dorset, UK). Self adhesive Magnet sheets were purchased from Polarity Magnets Company (UK). The peptide sequences (peptide 1 for *E. coli*: NH$_2$-Ahx-KVSRRRRRGGDKVDRRRRRGGD-Ahx-Cys (Seq Id #4); peptide 2 control NH$_2$-Ahx-ETKVEE-NEAIQK-Ahx-Cys (Seq Id #5); peptide 3 control NH2-Ahx-GGGAhx-Cys (Seq Id #6) and peptide 4 control C-Ahx-NMLSEVERE-SGSGSGSGSGS-COOH (Seq Id #7) were synthesised by PepmicCo., Ltd. (Suzhou, China). The self-adhesive tape was purchased from Whatman (London, UK). Nutrient agar and nutrient broth were purchased from (Oxoid, Amman, Jordan). Sterile filter 0.22 µm from Millipore, Amman, Jordan. The wash/storage buffer (10 mM Tris base, 0.15 M sodium chloride, 0.1% (w/v) bovine serum albumin, 1 mM ethylenediaminetetraacetic acid, 0.1% sodium azide, pH 7.5) and the coupling buffer (10 mM potassium phosphate, 0.15 M sodium chloride, pH 5.5) were prepared from chemicals of analytical grade.

Conjugation of the Peptide Substrates to Magnetic Bead

The magnetic bead suspension (1 ml) was mixed with the peptide (1.0 mg/mL), coupling agent EDC (0.57 mg/mL) and NHS (12 µg/mL). The mixture was shaken gently at room temperature for 24 hours. The uncoupled peptides were removed by washing the beads 3 times using wash buffer. Finally, the beads were stored at 4° C. in a storage buffer (Suaifan G A et al., 2012; Suaifan G A et al., 2013; Esseghaier C et al., 2014).

Gold Sensor Platform Preparation

The self-adhesive tape was coated with a thin layer of gold. After which, a narrow piece (~1.5-2×3 mm) was cut and stacked over the pH indicator plastic strip. This small strip was used as a physical support for the whole biofunctionalization process as well as the bacterial protease detection and quantification sensor (Suaifan G A et al., 2012; Suaifan G A et al., 2013; Esseghaier C et al., 2014).

Sensing Monolayer and Probe Immobilization

The gold sensing surface was mounted with the magnetic bead-peptide solution and allowed to stand at room temperature for 1 hour. After which, an external magnet (12.5× 12.5×5 mm) with a field-strength of 3360 gauss and 573 gauss at distance of 1 mm and 10 mm, respectively was passed over the functionalized strip to remove any unattached magnetic beads. A round permanent paper magnet was fixed on the strip back, at a distance of 2-3 mm below the gold sensor platform as shown in FIG. 1 (Suaifan G A et al., 2012; Suaifan G A et al., 2013; Esseghaier C et al., 2014).

Bacterial Strain Culturing

*Escherichia coli* (*E. coli* K-16) strain was streaked on a plate count agar and incubated at 37.0° C. for 24 h. One of the isolated colonies of *E. coli* K-16 was transferred into nutrient agar broth and incubated overnight at 37° C. The primary bacterial culture (PBC) concentration of *E. coli* was enumerated using the serial dilution and plate count method. The inoculums were diluted serially, and were saved for subsequent experiments.

Food Matrix Spiking and Proteases Preparation

Food samples (ground beef, turkey sausage, lettuce and milk) were obtained from a local grocery market in Amman-Jordan. Ground beef and turkey sausage were homogenized with sterile water at 1:5 (w:v) ratio in a blender for 1 min and then were rocked at room temperature for 2 hours. Lettuce leaves were rinsed with vegetable detergent, phosphate buffered saline (PBS; pH 7.4) and then cut into 4-$cm^2$ pieces using sterile scissor to remove any potential adulterates which may exist on the leafy surface.

Afterward, the PBC stock of *E. coli* was added to the food matrixes to create a 10-fold dilution samples. The spiked matrixes were allowed to incubate at room temperature (Medina M B et al., 2003) for 2 h and then clarified by centrifugation (5 min, 2000 rpm). The supernatant was then collected, centrifuged (10 min; 10,000×g) to sediment bacteria, and filtered through a 0.22 µm sterile filter. The crude sample filtrates containing bacterial secreted proteases were either used immediately or stored at −20° C. for later use. A positive control was prepared by creating 10-fold dilution from the PBC stock of *E. coli*. The number of bacteria was determined by plating 10-fold serial dilutions of the positive control (PBC) on the agar plates. Plates were incubated at 37° C. overnight and bacteria were then enumerated.

Biosensing of *E. coli* proteases

Figures 10A, 10B:
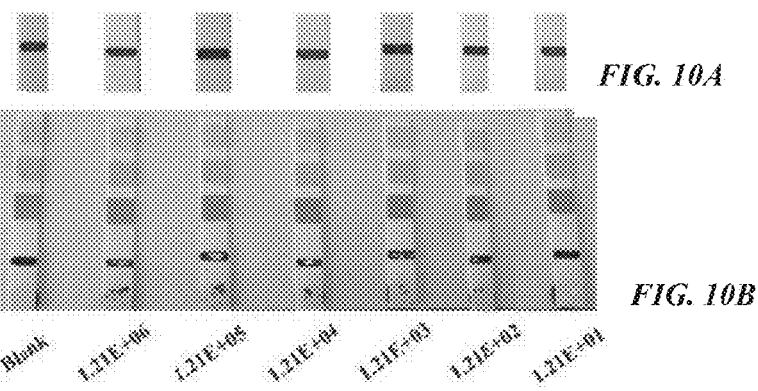
FIGS. 10A-10B Colorimetric *E. coli* sensor probe (specific *E. coli* substrate peptide covalently bound to a magnetic bead).

*E. coli* protease solution was down-streamed over the functionalized sensor platform. During the enzymatic cleavage reaction, the permanent magnets will attract the released magnetic beads prompting a visual observation for a qualitative evaluation of the tested samples (FIG. 1). Moreover, a powerful quantitative evaluation was possible using different concentrations of *E. coli* proteases solution ($1.21 \times 10^6$ CFU/mL, $1.21 \times 10^5$ CFU/mL, $1.21 \times 10^4$ CFU/mL, $1.21 \times 10^3$ CFU/mL, $1.21 \times 10^2$ CFU/mL, 121 CFU/mL) as shown in FIGS. 10A-10B.

Results and Discussion

Bacterial pathogens detection and identification relies upon culture of the organism, colony morphology evaluation, identification of characteristic nucleic acid sequences, biochemical markers and antigenic signatures associated with the microbe (Ivnitski D et al., 1999; Marusov G et al., 2012). However, these assays are complex, tedious, labor intensive and time-consuming (Siripatrawan U et al., 2006).

Nowadays, colorimetric assays have been of great importance for clinical and environmental diagnosis because of their simplicity and low cost. These assays are convenient because of the ease in qualitative detection using the naked eye without the need for a specific apparatus. However, quantitative detection of the color change is usually accomplished by using instruments such as spectrophotometer, epifluorescence microscope and luminescence counter. So far, a number of colorimetric detection methods for *E. coli* were reported. However, these assays require several preparation steps and the use of an instruments and trained personnel.

Colorimetric disposable biosensors which identify bacterial specific proteins, such as proteases that characterizes the presence of specific pathogenic microbe and thereby provides a marker for that microbe detection, in particular, those based on the degradation of a thin films (Hanumegowda N M et al., 2005) would provide a diagnostic tool for use in retail stores or home-use to detect contaminated food borne diseases. Therefore, in this disclosure we investigated the strength of implementing nanotechnology science within the field of biosensors for specific detection of *E. coli* K12.

Sensor Fabrication

The design of the colorimetric biosensor comprises a specific protease substrate coupled with a carboxyl-terminated magnetic beads that is covalently bound to the gold sensor surface. Upon proteolysis of the substrate-magnetic beads, colorimetric change would indicate the presence of the contaminating bacteria as described in FIG. 1. A specific peptide substrate was used in order to specifically detect the activities of *E. coli* proteases which have been considered a promising biomarker of food pathogen contamination. The biosensor consists of a peptide probe which is prepared by using specific *E. coli* peptide substrate sequence $NH_2$-Ahx-KVSRRRRRGGDKVDRRRRRGGD-Ahx-Cys, with aAhx-residue linker on either termini of the peptide. The N-terminal of the peptide was attached to the magnetic bead. The cysteine residue at the C-terminal, allows gold-sulfur interaction for the establishment of a self-assembled monolayer (SAM) of peptide and magnetic bead on the surface of the gold sensor (Suaifan G A et al., 2012; Esseghaier C et al., 2014; Suaifan G A et al., 2013).

Typically, the amount of protein that will compose a monolayer will depend upon factors such as the molecular weight (MW) of the protein substrate and its relative affinity for the bead as well as the surface area of the beads (Canterero L A et al., 1980). In our experiment we have found that the theoretical amount of protein calculated was substantially high. This could be attributed to the high efficiency of coupling process. Accordingly, a lower concentration was used to avoid any steric effects or nonspecific binding.

Magnetic beads-peptide solution was mounted over the gold surface and allowed to dry at room temperature to ensure proper functionalization of the gold sensor surface. After which, the golden color of the sensor surface chip became black as a result of complete immobilization. Later on, an external magnetic field was passed over the functionalized gold sensor surface to remove any non-immobilized magnetic bead. The sensor was then ready to for *E. coli* protease detection as shown in FIG. 1.

Sensor Testing

The proteolytic activity of the *E. coli* protease was analyzed by dropping the protease solution ($1.21 \times 10^6$ CFU/mL) over the functionalized gold sensor. The cleavage of the peptide-magnetic bead moiety from the sensor surface was accelerated by an external magnet. The dissociation of the black peptide-magnetic bead moiety from the gold sensor surface is followed by its attraction and will reveal the golden color of the sensor surface visible to the naked eyes as shown in FIGS. 10A-10B.

To gain some insight into a quantitative determination of the amount of *E. coli* protease present in solution. Different concentration of *E. coli* protease solutions ($1.21 \times 10^6$ CFU/mL, $1.21 \times 10^5$ CFU/mL, $1.21 \times 10^4$ CFU/mL, $1.21 \times 10^3$ CFU/mL, $1.21 \times 10^2$ CFU/mL, 12 CFU/mL) were dripped onto the functionalized gold sensor. A gradual increase in the visible bare gold area in a comparative way with protease solution concentration was observed. This is due to the proteolytic activity of the protease which results in the dissociation of the peptide-magnetic beads complex.

In view of our results, the developed sensor was able to detect as low as 12 CFU/mL without the use of any instrument and with an extraordinary short detection time of 30 seconds. Notably, different colorimetric sensors were previously developed. However, these methods do not fully satisfy the detection performance criteria since they are sophisticated and involve burdensome preparatory steps. For example, Quinônes B et al. (2011) designed a colorimetric detection method for *E. coli* O157 based on the use of DNA microarrays in combination with photopolymerization. The detection limit range was 100-1000 CFU/mL. Also, Villalobos P et al. (2012) reported the use of polymerized lipid vesicles as a colorimetric biosensor for detecting the presence of *E. coli* O157:H7 in water with a detection limit of over $10^8$ CFU. Detection sensitivity was improved through the use of cytochrome C peroxidase-encoding bacteriophage (Limit $10^7$ CFU/mL) (Hoang H et al., 2014) or by the application of aptamer based technique (aptasensor) (Limit $10^4$-$10^8$ CFU/mL) (Wu W et al., 2012). However, to the best of our knowledge and accessibility to literature resources the lowest limit of detection for *E. coli* O157:H7 was 7 CFU/mL by measuring the absorbance at 652 nm. This low sensitivity was achieved through using functionalized Au@Ptnano particles in about 40 min detection time (Su H et al., 2013).

Specificity Testing

Figure 11A:
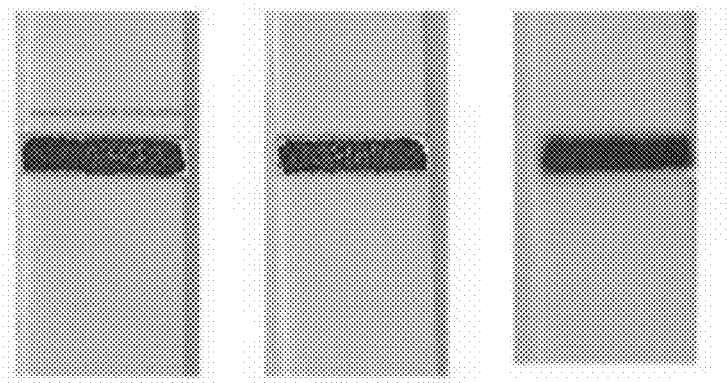
FIGS. 11A-11C Colorimetric *E. coli* protease sensor probe under the effect of other protease.
Figure 11B:
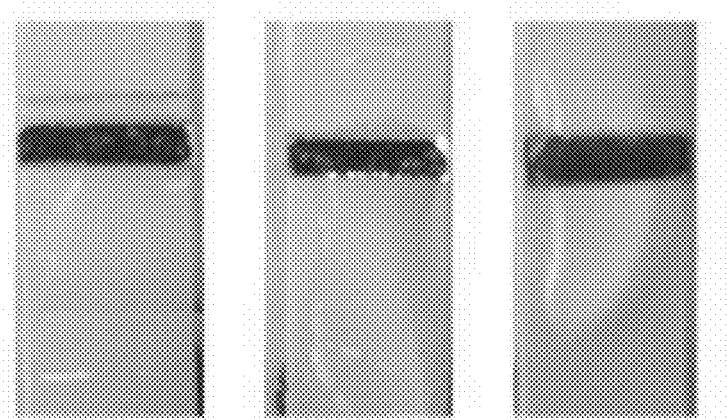
Figure 11C:
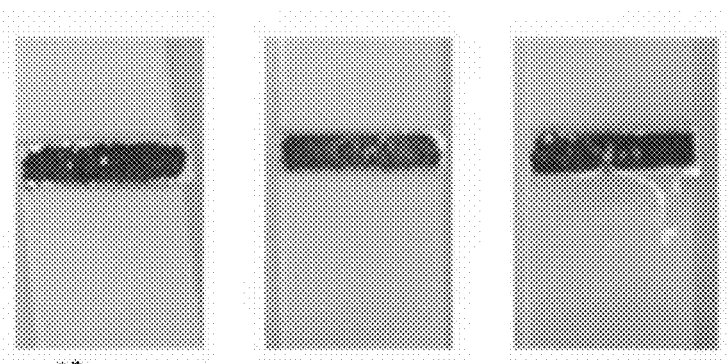

To assess the specificity of the biosensor we tested it in the presence of other food contaminating microbial proteases such as *Listeria, Pseudomonas* and *Staphylococcus aureus*. The sensor showed no disruption of the SAM layer and no significant change in the sensor surface golden color, showing sufficient detection specificity as shown in FIGS. 11A-11C.

Biosensor Detection of *E. coli* Spiked Food Matrices

Since our developed colorimetric biosensor was able to detect *E. coli*, we next determined its feasibility to detect *E. coli* in contaminated food products. Thus, fresh PBC of *E. coli* was spiked onto different food matrices including ground beef, turkey sausage, lettuce and milk. We first spiked 9 mL samples of different food product with 1.0 mL of fresh PBC of *E. coli* at eight bacterial concentrations range from $2.9 \times 10^8$ CFU/mL to $2.9 \times 10^1$ CFU/mL. A positive control was also prepared by spiking 9 mL of water with 1 mL of *E. coli* PBC. The control and the spiked samples were allowed to incubate at room temperature for 2 hours. After which *E. coli* was enumerated using the control sample. The samples were then centrifuged, filtered and examined on the developed biosensor. Clearly, a steady increase of the visible bare gold area in relation to bacterial concentration was observed. The developed biosensor displayed the ability to detect *E. coli* that was spiked in different food matrices with a low detection limit of 30 CFU/mL in ground beef, turkey sausage and lettuce, and a low detection limit of 300 CFU/mL in milk as shown in FIGS. 12A-12H. Thus, the developed biosensor is suitable for the detection of *E. coli* food contamination at the retail level and even at home.

Accordingly, this study has demonstrated the ability of the developed biosensor to detect *E. coli* proteases specifically and simultaneously in complex food matrices. The limit of detection was 12 CFU/mL in broth and 30-300 CFU/mL in food matrices. The assay was simple to perform, rapid, requires no sample pretreatment or pre-concentration and may be performed at the retail level to protect the consumer and at home. The detection mechanism does not require any labeling or amplification schemes. May be applied by anyone without the requirement of any sophisticated and expensive instrumentation. This novel, low-cost colorimetric method used covalently attached specific substrate-magnetic nano-carrier complexes. This biosensing configuration is amenable to an implementation for the qualitative and quantitative detection of *E. coli* proteases. The main advantage of the developed biosensor over existing technology is its ability to detect *E. coli* food contamination in less the 30 second and with a very low detection limit. This disclosure outlines a first step towards establishing a proof-of-concept biosensor for the detection of other microbial pathogens in contaminated food matrices without the use of sophisticated, expensive instruments and in a very short time. Thus, the biosensor of this disclosure presents a valuable tool not only for produce industry but also for agencies to better control potential risks associated with the consumption of contaminated foods.

Description of a Preferred Embodiment in Relation to *Porphyromonas gingivalis*

Materials and Reagents

Carboxyl-terminated beads of 50 nm diameter, N-hydroxysuccinimide (NHS), 1-(3-dimethylaminopropyl)-3-ethyl-carbodiimide (EDC) and the plastic pH indicator strip were purchased from Sigma Aldrich (Dorset, UK). Self-adhesive Magnet sheets were purchased from Polarity Magnets Company. The peptide sequences (substrate peptide COOH-Ahx-Arg-DLys-Ahx-Cys synthesised by Pepmic Co., Ltd. (Suzhou, China) and it was HPLC analysis the purity >98%. The self-adhesive tape was purchased from Whatman (London, UK). Brain heart infusion (BHI) medium and trypticase soy agar were purchased from sigma eldritch. Sterile filter 0.22 μm from Millipore sigma eldritch. The wash/storage buffer (10 mM Tris base, 0.15 M sodium chloride, 0.1% (w/v) bovine serum albumin, 1 mM ethylenediaminetetraacetic acid, 0.1% sodium azide, pH 7.5), the coupling buffer (10 mM potassium phosphate, 0.15 M sodium chloride, pH 5.5) were prepared from chemicals of analytical grade.

Preparation of *P. gingivalis* protease

*P. gingivalis* proteases were prepared as described previously (Kaman W E et al., 2012). In brief, *P. gingivalis* W50 was grown in brain heart infusion (BHI) medium under anaerobic conditions at 37° C. After 72 h of culturing, the bacteria were sedimented by centrifugation for 10 min at 10,000×g. The culture supernatant, containing secreted enzymes was filtered through a 0.22 μm sterile filter. After which, crude samples were used immediately or stored at −20° C. for later use.

The number of bacteria was determined by plating 10-fold serial dilutions on trypticase soy agar plates. Plates were incubated at 37° C. under anaerobic conditions, and bacteria were enumerated after 3 days of incubation. The culture was serially diluted in culture broth ($10^8$, $10^7$, $10^6$, $10^5$, $10\square$, $10^3$, $10^2$, and 10 CFU/ml), and 30 μl of each dilution was used to test the sensitivities of the substrates.

Conjugation of the *P. gingivalis* substrate peptide to magnetic bead

Magnetic bead suspension (1 ml) was mixed with the peptide (1.0 mg/mL), coupling agent EDC (0.57 mg/mL) and NHS (12 μg/mL). The mixture was shacked gently at room temperature for 24 hours. The uncoupled peptides were removed by washing the beads 3 times using wash buffer. Finally, the beads were stored at 4° C. in a storage buffer.

Gold Sensor Platform Preparation

Self-adhesive sheet was purchased from whatman (London, UK) and gold plated at cranfield university engineering department. The sheet was shredded into small stripes and stacked over a plastic strip at standardized distance. This plastic strip was used as a physical support for the whole biofunctionalization process as well as *P. gingivalis* protease detection and quantification sensor.

Sensing Monolayer and Probe Immobilization

The gold sensing surface was covered with the magnetic bead-peptide solution and allowed to stand at room temperature 30 minutes (FIG. 1). After which, an external magnet (12.5×12.5×5 mm) with field strength of 3360 gauss and 573 gauss at 1 mm and 10 mm distance, respectively was passed over the functionalized strip from a distance of 3 to 5 mm to remove any unattached magnetic beads. Round permanent paper magnet was fixed on the strip back, 2-3 mm distance below the gold sensor platform as shown in FIG. 1.

Saliva Collection and Spiking

Saliva was collected from one volunteer with no history of periodontal diseases under consistent conditions from 7:00 in the morning to the lunch time, with no eating and or smoking for 2 hours prior to collection. Saliva was then stored at −20° C. for later use. Spiking with *P. gingivitis* proteases (50 µl of saliva and 20 µl of various *P. gingivitis* proteases concentrations) was before application on the disposable sensor. Saliva sample was also spiked with culture broth as a negative control.

Examination of Periodontitis

To study the clinical applicability of the constructed sensor to diagnose *P. gingivalis* infections in situ, a swap from patient suffering from periodontitis was examined. This study was approved by the Institutional Ethical Board of the Academic Hospital Vrije Universiteit at Amsterdam, and informed consent was obtained from the donor.

Biosensing of *P. gingivalis* proteases

Figure 13A:
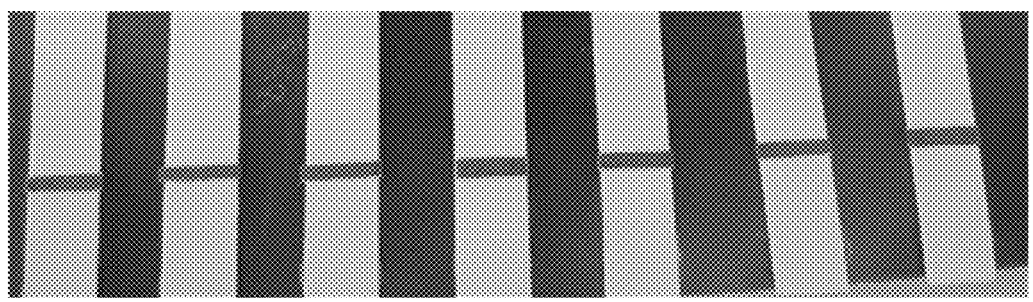
FIGS. 13A-13B (FIG. 13A): The blank sensor before the application of the protease (FIG. 13B): Colorimetric *P. gingivalis* protease sensor probe (specific *P. gingivalis* protease substrate peptide covalently bound to a magnetic bead) under the effect of different concentrations of *P. gingivalis* protease solutions.
Figure 13B:
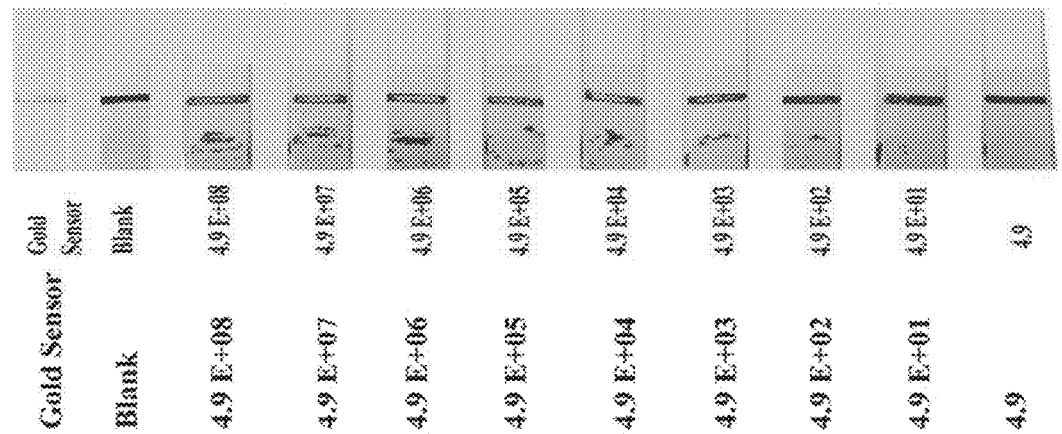

*P. gingivalis* proteases solution was down streamed over the functionalized sensor platform. During the enzymatic cleavage reaction, the permanent magnets will attract the released magnetic beads prompting a visual observation for a qualitative evaluation of the tested samples (FIG. 1). Moreover, a powerful quantitative evaluation was possible by using different concentrations of *P. gingivalis* proteases solution ($4.5 \times 10^8$ CFU/mL, $4.5 \times 10^7$ CFU/mL, $4.5 \times 10^6$ CFU/mL, $4.5 \times 10^5$ CFU/mL, $4.5 \times 10^4$ CFU/mL, $4.5 \times 10^3$ CFU/mL, $4.5 \times 10^2$ CFU/mL, 45 CFU/mL, 4.5 CFU/mL) as shown in FIGS. 13A-13B.

Results and Discussion

Accordingly, *P. gingivalis* is an invasive and evasive opportunistic oral pathogen. It invades periodontal tissues and evade the host defense mechanisms (Bostanci N et al., 2012; Jayaprakash K et al., 2014). In doing so, it utilizes a panel of virulence factors such as gingipains proteases which play a critical role in periodontal inflammation (Mysak J et al., 2014; Grayson R et al., 2003). In this way, *P. gingivalis* proteases gingipain are attractive indicator for periodontal diseases (Watanabe H et al., 1990). Notably, it is not only the amounts of this protease that differ in disease state, but also, and perhaps more importantly, the activity. Previously, Loesche and coworkers introduced enzyme based diagnostic technique for anaerobic periodontal infections based on plaque hydrolysis (Loesche W J et al., 1990; Loeshche W J et al., 1992). However, sophisticated instruments are requested. At present, very limited work is carried on specific gingpain proteases detection in periodontal disease.

Colorimetric disposable biosensors capable of selectively and specifically detect gingipain protease, in particular, those based on the degradation of a thin films (Hanumegowda N M et al., 2005; Zhou Y et al., 2006) would provide a diagnostic and monitoring technique for periodontal diseases (Saum A G et al., 2000). Therefore, in this article we investigated the power of implementing nanotechnology science within the field of biosensors for specific detection of gingpain. The designed biosensors will be based on the detection of the amidolytic activity of *P. gingivalis* protease in patient saliva as an easily accessible biochemical fluid.

The colorimetric biosensor is easily fabricated paper-based sensors which consists of a peptide probe prepared by using specific peptide substrate (Kaman W E et al., 2012), with a Ahx residue linker on either termini of the peptide. The D-amino acid was added to the peptide sequence as it has been found to facilitate rapid identification of prokaryotic proteases that possess novel cleavage patterns (Kaman W E et al., 2012). The N-terminal of the peptide was attached to the magnetic bead. A cysteine residue was added at the C-terminal, allowing a gold-sulfur interaction for the establishment of a self-assembled monolayer (SAM) of peptide and magnetic bead on the surface of the gold sensor (Suaifan G A et al., 2012; Suaifan G A et al., 2013; Esseghaier C et al., 2014). The magnetic beads-peptide solution was mounted over the gold surface and allowed to dry at room temperature to ensure proper functionalization of the gold sensor surface. After which, the golden color of the sensor surface chip turn out to be black as a result of complete immobilization. Later on, an external magnetic field was passed over the functionalized gold sensor surface to remove any non-immobilized magnetic bead. The sensor was then ready to for *P. gingivalis* protease detection as shown in FIG. 13A.

Sensor Testing

The proteolytic activity of *P. gingivalis* protease was analyzed by dropping protease solution ($4.9 \times 10^8$ CFU/mL) over the functionalized gold sensor. The cleavage of the peptide-magnetic bead moiety from the sensor surface was accelerated by an external magnet. The dissociation of the peptide-magnetic bead moiety from the gold sensor surface caused the destabilization of the blocking organic/metallic monolayer, revealing the golden color of the of sensor surface visible to the naked eyes as shown in FIG. 1.

To gain some insight into a quantitative determination of the amount of *P. gingivalis* protease present in solution. The functionalized gold sensor was dripped with *P. gingivalis* protease solutions of different concentration ($4.5 \times 10^8$ CFU/mL, $4.5 \times 10^7$ CFU/mL, $4.5 \times 10^6$ CFU/mL, $4.5 \times 10^5$ CFU/mL, $4.5 \times 10^4$ CFU/mL, $4.5 \times 10^3$ CFU/mL, $4.5 \times 10^2$ CFU/mL, 45 CFU/mL, 4.5 CFU/mL). A gradual increase in the visible bare gold area in comparative way with protease solution concentration was observed. This is due to the proteolytic activity of the protease which results in the dissociation of the peptide-magnetic beads complex from the sensor surface as shown in FIGS. 13A-13B. Accordingly, the designed sensor showed a very high sensitivity with a lower detection limit of 4.9 CFU/mL in 20 second time. In view of our results, the constructed sensor showed a detection limit lower than the previously reported (Kaman W E et al., 2012).

Saliva Testing

Figures 14A, 14B, 14C:
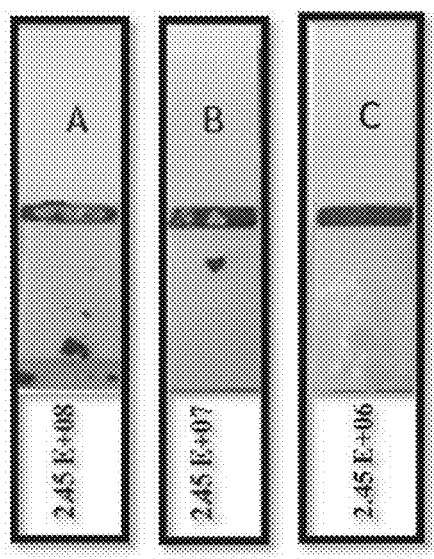
FIGS. 14A-14C Colorimetric *P. gingivalis* protease sensor probe under the effect of different concentrations of *P. gingivalis* protease spiked in saliva, blank sensor.

The feasibility of the constructed sensor was examined by using saliva as an oral diagnostic fluid for the detection of *P. gingivalis* infections under a reliable non laboratory assay. Accordingly, different *P. gingivalis* protease concentrations ($4.5 \times 10^8$ CFU/mL, $4.5 \times 10^7$ CFU/mL, $4.5 \times 10^6$ CFU/mL) were spiked into saliva sample provided by an individual with no history of periodontal diseases in a 1:1 aliquots ratio as shown in FIGS. 14A-14C. Each concentration was added over the functionalized gold sensor under the effect a permanent magnet attached to the back of the strip. Clearly, a steady increase of the visible bare gold area in relation with the protease concentration was observed (FIG. 14A and FIG. 14B). Unspiked saliva sample was applied as a negative control and proved no cleavage of the magnetic beads-peptide with no disruption of the SAM layer and no significant change in the sensor surface golden color (FIG. 14C). Interestingly, the developed sensor is suitable for the analysis of patient s specimens at the site of collection enabling dental practitioner to perform a "on-site" test to identify the periodontal pathogens *P. gingivalis*. The observed LOD was $2.45 \times 10^6$ CFU/mL and was lower than the reported LOD in a previous study (Kaman W E et al., 2012).

Patient Sample Testing

Figures 15A, 15B:
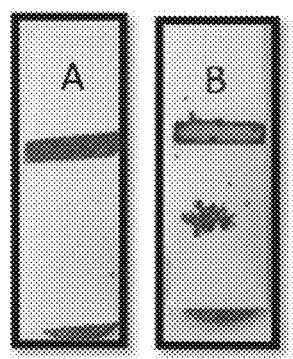
FIGS. 15A-15B Colorimetric *P. gingivalis* protease sensor probe application on patient sample.

To evaluate the performance characteristics and the clinical applicability of the novel sensor optimized to diagnose *P. gingivalis* infections in situ, a specimen from patient suffering from periodontitis with *P. gingivalis* culture positive was examined. As a gold standard, periodontal pathogen was identified by routine culture as described previously (Kaman W E et al., 2012). A clear positive result was obtained. Notably, the visible golden color of the sensor surface was clear to the naked eye as shown in FIGS. 15A-15B.

Figures 16A, 16B:
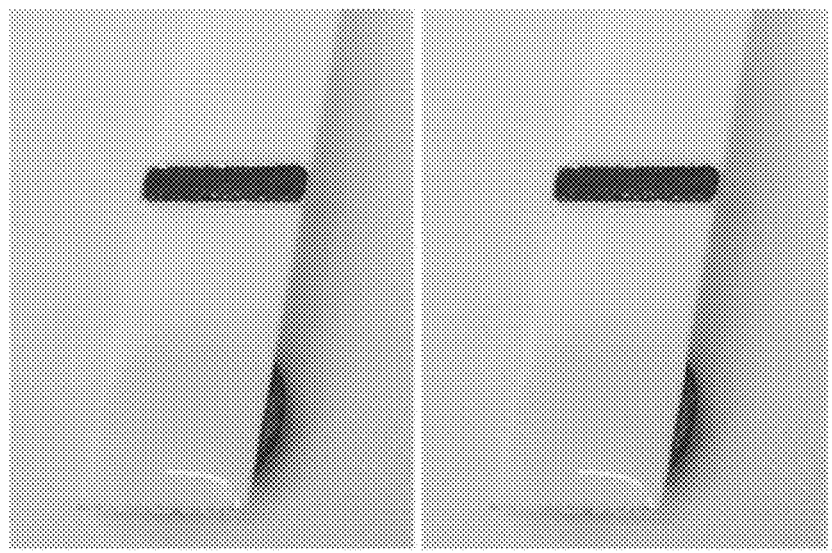
FIGS. 16A-16B Colorimetric *P. gingivalis* protease sensor probe under the effect of *Listeria* protease.
Figure 17:
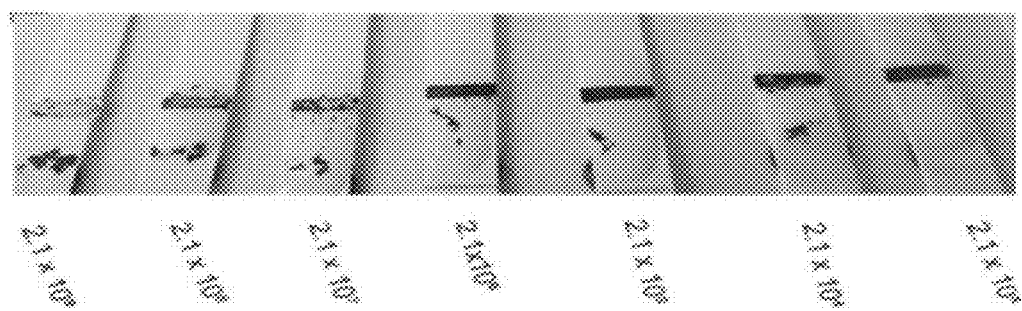
FIG. 17 Sensitivity of the sensor.
Figure 18:
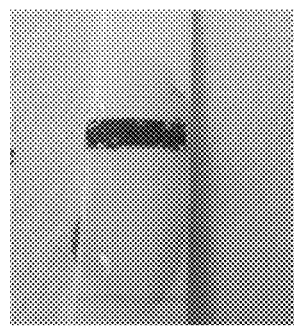
FIG. 18 Specificity of the sensor.

Likewise, the specificity of the biosensor in the presence of *Listeria monocytogenes* protease was assessed. The sensor showed no disruption of the SAM layer and no significant change in the sensor surface golden color, showing sufficient detection specificity as shown in FIGS. 16A-16B.

Accordingly, among proteases, *P. gingivalis* proteases have been of significant interest because they are considered as one of the promising biomarkers in association with periodontal diseases. The use of an enzyme based diagnostic tool based on the presence of *P. gingivalis* gingipain was previously described (Kaman W E et al., 2012; Loeasche W J et al., 1990; Loeasche W J et al., 1992). However, the sensitivity achieved was 10-folds lower, i.e., $10^7$ than our current results. Also, these reported diagnostic tools require the use of sophisticated instrument and trained personnel.

Furthermore, in this disclosure, we imply a novel and low-cost colorimetric method capable of detecting *P. gingivalis* using covalently attached gingipain specific substrate-magnetic nano-carrier complexes. This biosensing configuration is amenable to an implementation for the qualitative and quantitative detection of *P. gingivalis* proteases as periodontitis diagnostics technique. Assay may be performed on site by non-specialized personal without the requirement of any sophisticated expensive instrumentation. The detection mechanism does not require any labeling or amplification schemes. Noteworthy, *P. gingivalis* protease detection is based on the appearance of the gold sensor surface golden color. The golden color is simply observed by the naked eyes. The limit of detection achieved in saliva was as low as $2.45 \times 10^6$ CFU/mL.

Description of a Preferred Embodiment in Relation to *Listeria monocytogens* (*L. monocytogens*)

Material and Method

Bacteria

*Listeria monocytogenes* (murray et al) pirie ATCC 19115 grown in 5 ml Brain heart infusion purchased from Sigma Aldrich UK incubated at 37° C. for 18 hours from this suspension 10-folds serial dilution was done the concentration of the original stocks by using viable count of spread dilution method. Consequently the bacteria were pelted by centrifuged at 3000×g for 10 minutes to get the protease for each dilution. The supernatant was filtered with sterile syringe filter 0.2 μm from Millipore from Sigma Aldrich UK.

Peptide Sequence

Specific peptide sequence known to be cleaved specifically by *Listeria monocytogenes* (Mitchell C et al., 2003) is synthesized upon request from Pepmic Co., Ltd. (Suzhou, China) peptide 1: C-Ahx-nmlsevere-SGSGSGSGSGS-COOH (Seq Id #8) elongated with D-amino acid (Zhang D et al., 2009) peptide 2: C-Ahx-NMLSEVERE-SGSGSGSGSGS-COOH without D-amino acid, known that D-amino is specific and facilitate the prokaryotic cleavage, with purity of about 90%. The identity of the substrate was confirmed by spectrometry. The peptide was provided in lyophilized form we diluted with distilled water and kept at −4° C.

Magnetic Beads

Carboxyl-terminated beads of 50 nm in diameter, N-hydroxysussinimide (NHS), 1-(3-dimethylaminopropyl)-3-ethyl-carbodiimide (EDC) are purchased from Sigma Aldrich, suspended in a storage buffer (10 mM Tris, 0.15 M NaCl, 0.1% (w/v) bovine serum albumin (BSA), 1 mM ethylenediaminetetraacetic acid (EDTA), 0.1% sodium azide, adjusted pH 7.5). Strips were purchased from Sigma Aldrich (Dorest, UK)

Coupling buffer (10 mM potassium phosphate, 0.15 M sodium chloride, pH 5.5) and wash/storage buffer (10 mM potassium phosphate, 0.15 M sodium chloride 0.1% (w/v) bovine serum albumin. 1 mM Ethylenediaminetetraactic, 0.1% sodium azide pH 7.5 were prepared from chemicals of analytical grade.

Conjugation of the *Listeria monocytogens* Substrate Peptide to Magnetic Neads

After washing magnetic beads (1 mL) and preparation of peptide substrate, coupling agent EDC (0.57 mg/mL) and NHS (12 mg/mL) will be prepared and added to magnetic beads immediately (unstable reagent) and then add peptide (1.0 mg/mL). The mixture was shaken gently at room temperature for 24 hours. The uncoupled peptides were removed by washing the beads 3 times with washing buffer. Finally, the beads were stored at 4° C. in storage buffer.

Preparation of the Gold Sensor Platform

Self-adhesive tape was purchased from Whatman (London, UK) sheet will be gold plated at canfield university engineering department. The sheet will be cut by sharp high quality blade to get even edge 1 mm depth 1 cm width, then stacked it on the plastic strip at standardized distance.

Immobilization of Sensing Monolayer

The magnetic beads peptide solution will be mixed genteelly and transfer with specific amount to cover the gold sensing surface completely. Consequently after the complete attachment of the beads peptide substrate with the gold surface, permanent magnetic size (12.5×12.5×5 cm), strength (3360 gauss and 573 gauss) will be applied with 5-10 mm distance to remove un-immobilized beads.

The golden surface color will be changed from gold to black due to complete immobilization of the gold sensor.

Standardized the Paper Magnetic

Self-adhesive magnetic sheets were provided from Polarity Magnetic Company, it was localized at the back of the strip with standardized size 1 cm diameter at 1 cm from the functionalized sensor. It works as detection and collection of the cleavage peptide sequence beads.

Bio Sensing of *Listeria monocytogens* Protease

The strip is ready to test the proteolytic activity of the protease enzyme produced from the *Listeria monocytogenes*, the protease will be added as drop 20 μl over the sensor, cleavage of the peptide-magnetic beads was detected and the intensity of the cleavages is proportional to the concentration of the protease result in expose the gold back ground and accumulation of the cleaved peptide magnetics beads at the permanent magnetic area indorsing a visual colorimetric detection for qualitative evaluation of the tested sample FIG. 1.

Preparation of the Sample

Fresh full fat milk provided from a diary company in UK and ready to eat meat was purchased and minced with 5 ml sterile water, are tested directly without centrifugation with the sensor to check the effect of the milk and meat content on the sensor.

Spiking the Food 5 ml of the whole fat milk is inoculated with a colony of the *Listeria monocytogenes* incubated 35° C. from 15-18 hours. The sensor were tested with sample directly and after centrifuged 10.000×g, the supernatant, containing protease was sterilized by filtration with 0.2 μm filter (Sigma UK) the sample used immediately.

2 gram of ready to eat meat are minced with 5 ml of sterile water vortex for 2 minutes to homogenized the sample, the meat inoculated with *Listeria monocytogens* incubated 3° C. from 15-18 hours. The sensors were tested with sample directly and after centrifuged 10.000×g, the supernatant, containing protease was sterilized by filtration with 0.2 μm filter (Sigma UK) the sample used immediately.

Results and Discussion

Proteases are enzymes involved in the bacterial growth, multiplication, and pathogenicity. Thus, the focus on the protease enzyme with power of implementing of nanoparticles as screening diagnostic tool that will result in reaching the Point-Of-Care. Colorimetric disposable paper based biosensor is easily to be fabricated, on site portable low coast, without the use of instrument.

In this study based on the hypothesis of the specificity of the D-amino acid to detect the proteolytic activity of prokaryotic and the novel detection of specific peptide sequence to be cleaved specifically by *Listeria monocytogens* from Mitchell C S (Kaman W E et al., 2003).

We developed portable low cost screening detection method for *Listeria monocytogens* detection.

Detection of the Sensitivity of the Sensor

Serial dilution of the protease was made to get the lower detection concentration of the colony in the sample. The protease was applied to two peptide sequence peptide 2 without elongation with the D-amino acid, peptide 1 with the elongation with the D-amino acid the result shows that peptide 1 shows more specific cleavage with lower detection concentration of 2107 CFU/ml where in peptide 2 the cleavage was poor and this is due to the limited elongation of the peptide sequence that gives space for the protease to act with the consideration of the undesired length that may give false positive ((Kaman W E et al., 2003). There was clear visible correlation between the protease concentration and cleavage that are represented by the intensity of the magnetic particles accumulate at the paper magnetic area and the gradual increase in the appearance of the gold background (FIG. 17)

Testing the Specificity of the Sensor

The sensor was tested for the specificity by using the protease of *Staphylococcus aureus* and *Bacillus anthrax*. The results show no cleavage with both protease compare to the clear cleavage when used with the *listeria* protease (FIG. 18).

Testing the Sensor with the Food

The sensor was tested with supernatant of the ready to eat food to check that the food has any proteolytic activity that might affect the results and it shows there is no effect.

Testing the Spiked Food

Fresh whole milk and ready to eat meat were spiked with the colony of *Listeria monocytogenes* incubated at 35° C. for 15-18 hours. The stock concentration was detected by 10-fold serial dilution and viable count of spread dilution method the original stock of the meat was 13.8×10ω CFU/ml and fresh whole milk stock count was 11.7×10ω. The sample were tested with sensor pre-centrifuged and after centrifuged the by dripping the sample over the senor with standardized amount results shows that concentration of the protease gives clear visible reaction.

As will be understood by a skilled person, the sensor and associated detection method of the present disclosure may be applied to the detection of other pathogens not specifically referred to herein. Accordingly, the specification and drawings are to be regarded in an illustrative rather than a restrictive sense.

Although the present embodiments have been described with reference to specific example embodiments, it will be evident that various modifications and changes may be made to these embodiments without departing from the broader spirit and scope of the various embodiments.

INDUSTRIAL APPLICABILITY

The sensor and associated detection method is simple, sensitive, specific, rapid, cost-effective. A sample analyzed using the sensor and detection method of this disclosure may be of various origins. For example, the sample may be of biological origin, of clinical origin, from food, from a chemical plant, from an industrial plant, from a hospital, from school, from the environment.

What is claimed is:

1. A biosensor for detecting a pathogen in a sample, comprising:
a planar support having two sides, a first surface and a second surface, the second surface located on an opposite side from the first side and from the first surface;
a particle support attached to a first top surface of the planar support as a small strip, the particle support being of a first color, wherein the particle support is a gold surface and is located upstream of a magnetic material;
the magnetic material attached to a second bottom surface of the planar support, spaced apart and downstream from the particle support;
a plurality of magnetic particles of a second color different from the first color, each particle being attached to the particle support through a chemical substrate specific to the pathogen to be detected, a first end of the chemical substrate being attached to one of the magnetic particle and a second end of the chemical substrate being attached to the particle support,
an external magnetic source is applied by holding another magnet over the particle support and slowly moving the external magnet in the direction of the planar support downstream towards the magnetic material that is spaced apart and downstream away from the particle surface to separate the attached and an unattached magnetic particle to create a visible field between the particle support and the magnetic material on the planar surface to detect the presence or absence of the pathogen in the sample.

2. The sensor of claim 1, wherein the magnetic particles are nanoparticles.

3. The sensor of claim 1, wherein the planar support is of plastic material, or is dielectric, or is a piece of paper, or is a piece of cloth.

4. The sensor of claim 1, wherein the particle support is of metal material, or of plastic material, or is dielectric, or is a piece of paper, or is a piece of cloth.

5. The sensor of claim 1, comprising two or more particle supports.

6. The sensor of claim 1, wherein the chemical substrate is a peptide substrate that may be cleaved by the pathogen.

7. The sensor of claim 1, further comprising a first linker between the first end of the chemical substrate and the magnetic particle and a second linked between the second end of the chemical substrate and the particle support, the first and second linkers being the same or different.

8. The sensor of claim 1, comprising two or more particle supports, of the same color or of different colors.

9. The sensor of claim 1, comprising first and second particle supports, wherein a first set of magnetic particles attached to the first particle support is of a color, and a second set of magnetic particles attached to the second particle support is of another color.

10. The sensor of claim 1, comprising first and second particle supports, wherein a first chemical substrate attached to the first particle support is specific to a pathogen, and a second chemical substrate attached to the second particle support is specific to another pathogen.

11. The sensor of claim 1, wherein the pathogen is selected from the group consisting of *Pseudomonas aeruginosa, Staphyloccocus aureus, Escherichia coli, Porphyromonas gingivalis* and *Listeria monocytogens*.

12. The sensor of claim 1, wherein the sample is of biological origin, of clinical origin, from a patient, from food, from a chemical plant, from an industrial plant, from a hospital, from a school or from the environment.

13. The sensor of claim 1, which is disposable.

* * * * *